(12) United States Patent
Asakura et al.

(10) Patent No.: US 8,293,505 B2
(45) Date of Patent: Oct. 23, 2012

(54) L-AMINO ACID-PRODUCING MICROORGANISM AND A METHOD FOR PRODUCING AN L-AMINO ACID

(75) Inventors: Yoko Asakura, Kawasaki (JP); Yuri Nagai, Kawasaki (JP); Takuji Ueda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 154 days.

(21) Appl. No.: 12/258,630

(22) Filed: Oct. 27, 2008

(65) Prior Publication Data
US 2009/0104667 A1 Apr. 23, 2009

Related U.S. Application Data

(63) Continuation of application No. PCT/JP2007/058941, filed on Apr. 25, 2007.

(30) Foreign Application Priority Data

Apr. 28, 2006 (JP) ................................ 2006-124692

(51) Int. Cl.
*C12Q 1/10* (2006.01)
*C12P 21/06* (2006.01)
*C12P 13/04* (2006.01)

(52) U.S. Cl. .......................... 435/106; 435/38; 435/69.1

(58) Field of Classification Search .................... None
See application file for complete search history.

(56) References Cited

U.S. PATENT DOCUMENTS

| | | | |
|---|---|---|---|
| 4,286,060 A * | 8/1981 | Gluschenko et al. | 435/110 |
| 4,772,557 A * | 9/1988 | Eisen et al. | 435/320.1 |
| 5,053,328 A * | 10/1991 | Muetze et al. | 435/106 |
| 5,175,107 A | 12/1992 | Debabov et al. | |
| 5,213,972 A * | 5/1993 | McCandliss et al. | 435/89 |
| 5,393,671 A | 2/1995 | Tujimoto et al. | |
| 5,573,945 A | 11/1996 | Ono et al. | |
| 5,661,012 A | 8/1997 | Sano et al. | |
| 5,688,671 A | 11/1997 | Sugimoto et al. | |
| 5,827,698 A | 10/1998 | Kikuchi et al. | |
| 5,830,716 A | 11/1998 | Kojima et al. | |
| 5,908,768 A | 6/1999 | Ono et al. | |
| 5,932,453 A | 8/1999 | Kikuchi et al. | |
| 6,040,160 A | 3/2000 | Kojima et al. | |
| 6,110,714 A | 8/2000 | Matsui et al. | |
| 6,132,999 A | 10/2000 | Debabov et al. | |
| 6,303,348 B1 | 10/2001 | Livshits et al. | |
| 6,319,696 B1 | 11/2001 | Kishino et al. | |
| 6,991,924 B2 * | 1/2006 | Ptitsyn et al. | 435/114 |
| 7,186,531 B2 | 3/2007 | Akhverdian et al. | |
| 7,306,933 B2 | 12/2007 | Van Dien et al. | |
| 2002/0025564 A1 | 2/2002 | Kobayashi et al. | |
| 2002/0110876 A1 | 8/2002 | Miyata et al. | |
| 2002/0160461 A1 | 10/2002 | Nakai et al. | |
| 2004/0132165 A1 | 7/2004 | Akhverdian et al. | |
| 2005/0009151 A1 * | 1/2005 | Chase et al. | 435/106 |
| 2005/0239177 A1 | 10/2005 | Livshits et al. | |
| 2006/0019355 A1 | 1/2006 | Ueda et al. | |
| 2006/0088919 A1 | 4/2006 | Rybak et al. | |
| 2006/0160191 A1 | 7/2006 | Kataoka et al. | |
| 2006/0216796 A1 | 9/2006 | Hashiguchi et al. | |
| 2007/0004014 A1 | 1/2007 | Tsuji et al. | |

FOREIGN PATENT DOCUMENTS

WO WO2006/038695 4/2006

OTHER PUBLICATIONS

Pierard et al., 1976, Journal of Bacteriology, 127: 291-301.*
Loh et al., 2006, PNAS, USA, 103: 5114-5119.*
International Report on Patentability for PCT Patent App. No. PCT/JP2007/058941 (Nov. 27, 2008).
Bonekamp, F., et al., "Mechanism of UTP-modulated attenuation at the *pyrE* gene of *Escherichia coli*: an example of operon polarity control through the coupling of translation to transcription," The EMBO Journal 1984;3(12):2857-2861.
Jensen, K. F., et al., "Attenuation at nucleotide biosynthetic genes and amino acid biosynthetic operons of *Escherichia coli*," TIBS 1986;11(9):362-365.
Liu, C., et al., "Multiple Control Mechanisms for Pyrimidine-Mediated Regulation of *pyrBI* Operon Expression in *Escherichia coli* K-12," J. Bacteriol. 1989;171(6):3337-3342.
Supplemental European Search Report from European Patent App. No. 07742376.2 (May 26, 2009).
An, G., et al., "Cloning the *spoT* Gene of *Escherichia coli*: Identfication of the *spoT* Gene Product," J. Bacteriol. 1979;137(3):1100-1110.
Andersen, J. T., et al., "Attenuation in the *rph-pyrE* operon of *Escherichia coli* and processing of the dicistronic mRNA," Eur. J. Biochem. 1992;206:381-390.
Bayles, D. O., et al., "Sequence of phylogenetic analysis of the *Rhizobium leguminosarum* biovar *trifolii pyrR* gene, overproduction, purification and characterization of orotate phosphoribosyltransferase," Gene 1997;195:329-336.
Bunnak, J., et al., "Orotate Phosphoribosyltransferase from *Thermus thermophilus*: Overexpression in *Escherichia coli*, Purification and Characterization," J. Biochem. 1995;118: 1261-1267.
Jensen, K. F., "The *Escherichia coli* K-12 "Wild Types" W3110 and MG1655 Have an *rph* Frameshift Mutation That Leads to Pyrimidine Starvation Due to Low *pyrE* Expression Levels," J. Bacteriol. 1993;175(11):3401-3407.
Jensen, K. F., et al., "Overexpression and Rapid Purification of the *orfE/rph* Gene Product, Rnase PH of *Escherichia coli*," J. Biol. Chem. 1992;267(24):17147-17152.
Poulsen, P., et al., "Nucleotide sequence of the *Escherichia coli pyrE* gene and of the DNA in front of the protein-coding region," Eur. J. Biochem. 1983;135:223-229.
International Search Report for PCT Patent App. No. PCT/JP2007/058941 (Jun. 19, 2007).

* cited by examiner

*Primary Examiner* — Joanne Hama
(74) *Attorney, Agent, or Firm* — Shelly Guest Cermak; Cermak Nakajima LLP

(57) ABSTRACT

An L-amino acid is produced by culturing a microorganism which belongs to the family Enterobacteriaceae and is able to produce an L-amino acid, wherein the bacterium has been modified to enhance orotate phosphoribosyltransferase activity is enhanced, in a medium to produce and cause accumulation of an L-amino acid in the medium or cells, and collecting the L-amino acid from the medium or the cells.

10 Claims, No Drawings

L-AMINO ACID-PRODUCING MICROORGANISM AND A METHOD FOR PRODUCING AN L-AMINO ACID

This application is a continuation under 35 U.S.C. §120 to PCT Patent Application No. PCT/JP2007/058941, filed on Apr. 25, 2007, which claims priority under 35 U.S.C. §119 to Japanese Patent Application No. 2006-124692, filed Apr. 28, 2006, both of which are incorporated by reference. The Sequence Listing filed electronically herewith is also hereby incorporated by reference in its entirety (File Name: US-378_Seq_List; File Size: 18 KB; Date Created: Oct. 27, 2008).

BACKGROUND OF THE INVENTION

1. Field of the Invention

The present invention relates to a method for producing an L-amino acid using a microorganism, and especially relates to a method for producing L-amino acids such as L-lysine, L-threonine, and L-glutamic acid. For example, L-lysine and L-threonine are industrially useful as additives for animal feed, ingredients in health foods, amino acid infusions, and so forth, and L-glutamic acid is useful as a seasoning.

2. Brief Description of the Related Art

L-amino acids are industrially produced by fermentation using microorganisms belonging to the genera *Brevibacterium, Corynebacterium, Escherichia*, and the like. For example, methods for producing L-lysine include those disclosed in European Patent No. 0643135, European Patent No. 0733712, European Patent Publication No. 1477565, European Patent Publication No. 0796912, European Patent Publication No. 0837134, International Patent Publication WO01/53459, European Patent Publication No. 1170376, and International Patent Publication WO2005/010175.

In such methods, strains isolated from the nature or artificially produced variant strains are used. Furthermore, microorganisms which have been modified by recombinant DNA techniques to increase the activities of enzymes involved in basic L-amino acid biosynthesis, and so forth are used.

Orotate phosphoribosyltransferase [EC:2.4.2.102.10] is an enzyme of the pyrimidine biosynthesis system, and is encoded by the pyrE gene. The pyrE gene is present on an operon with rph, which encodes RNase PH. The rph gene is located upstream relative to the pyrE gene. In the *Escherichia coli* MG1655 or W3110 strain, the coding region of the rph contains a −1 frameshift in the 3' end region, which results in insufficient expression of pyrE and causes pyrimidine starvation (Journal of Bacteriology, vol. 175, June 1993, p 3401-3407).

However, there have been no reports concerning the relationship between the expression of the rph-pyrE operon, the amount of the pyrE gene product which is expressed, orotate phosphoribosyltransferase activity, and substance production by *Enterobacteria*.

SUMMARY OF THE INVENTION

The present invention describes a bacterial strain belonging to the family Enterobacteriaceae which is capable of efficiently producing an L-amino acid, and a method for efficiently producing an L-amino acid using the strain. It has been found that L-amino acids can be efficiently produced by using a microorganism which has enhanced orotate phosphoribosyltransferase activity.

The present invention thus provides the following:

It is an aspect of the present invention to provide a microorganism which belongs to the family Enterobacteriaceae and is able to produce an L-amino acid, wherein the bacterium has been modified to enhance orotate phosphoribosyltransferase activity.

It is a further aspect of the present invention to provide the microorganism as described above, wherein the orotate phosphoribosyltransferase activity is enhanced by a method selected from the group consisting of: A) increasing the expression of the pyrE gene which encodes orotate phosphoribosyltransferase, B) increasing the translation of orotate phosphoribosyltransferase, and C) combinations thereof.

It is a further aspect of the present invention to provide the microorganism as described above, wherein the orotate phosphoribosyltransferase activity is enhanced by a method selected from the group consisting of: A) increasing the copy number of the pyrE gene which encodes orotate phosphoribosyltransferase, B) modifying an expression control sequence of said gene, and C) combinations thereof.

It is a further aspect of the present invention to provide the microorganism as described above, in which the rph-pyrE operon has been modified, and wherein the orotate phosphoribosyltransferase activity is enhanced by the introduction of a mutation which suppresses a native −1 frameshift mutation in the coding region of the rph gene.

It is a further aspect of the present invention to provide the microorganism as described above, wherein the orotate phosphoribosyltransferase activity is enhanced by deletion of the attenuator which is located upstream of the pyrE gene.

It is a further aspect of the present invention to provide the microorganism as described above, wherein said orotate phosphoribosyltransferase is a protein selected from the group consisting of:

(A) a protein comprising the amino acid sequence of SEQ ID NO: 12, (B) a protein comprising the amino acid sequence of SEQ ID NO: 12, but which includes substitutions, deletions, insertions, additions, or inversions of one or several amino acid residues, and has orotate phosphoribosyltransferase activity.

It is a further aspect of the present invention to provide the microorganism as described above, wherein the pyrE gene is selected from the group consisting of:

(a) a DNA comprising the nucleotide sequence of nucleotides 782 to 1423 of SEQ ID NO: 11, (b) a DNA which is able to hybridize with a nucleotide sequence complementary to the nucleotide sequence of nucleotides 782 to 1423 of SEQ ID NO: 11, or a probe which can be prepared from the nucleotide sequence, under stringent conditions, and encoding a protein having orotate phosphoribosyltransferase activity.

It is a further aspect of the present invention to provide the microorganism as described above, wherein the L-amino acid is selected from the group consisting of L-lysine, L-arginine, L-histidine, L-isoleucine, L-valine, L-leucine, L-threonine, L-phenylalanine, L-tyrosine, L-tryptophan, L-cysteine, L-glutamic acid, and combinations thereof.

It is a further aspect of the present invention to provide the microorganism as described above, wherein the microorganism belongs to a genera selected from the group consisting of *Escherichia, Enterobacter*, and *Pantoea*.

It is yet another aspect of the present invention to provide a method for producing an L-amino acid, which comprises A) culturing the microorganism as described above in a medium, and collecting the L-amino acid from the medium or the cells.

It is a further aspect of the present invention to provide the method as described above, wherein glycerol is present in the medium as the carbon source.

It is a further aspect of the present invention to provide the method as described above, wherein the L-amino is selected from the group consisting of L-lysine, L-arginine, L-histidine, L-isoleucine, L-valine, L-leucine, L-threonine, L-phenylalanine, L-tyrosine, L-tryptophan, L-cysteine, L-glutamic acid, and combinations thereof.

DESCRIPTION OF THE PREFERRED EMBODIMENTS

<1> Microorganism

The microorganism is a bacterium belonging to the family Enterobacteriaceae and is able to produce an L-amino acid, wherein the bacterium has been modified so that orotate phosphoribosyltransferase activity is enhanced. The ability to produce an L-amino acid (L-amino acid-producing ability) means the ability of the microorganism to produce and cause accumulation of an L-amino acid in a medium or cells to such an extent that the L-amino acid can be collected from the medium or cells when the microorganism is cultured in the medium. The microorganism may be able to produce two or more kinds of L-amino acids. Although the microorganism may inherently be able to produce an L-amino acid, it may also have been modified using recombinant DNA techniques so that it can produce the L-amino acid.

Although the type of the L-amino acid is not particularly limited, examples include basic amino acids such as L-lysine, L-ornithine, L-arginine, L-histidine and L-citrulline, aliphatic amino acids such as L-isoleucine, L-alanine, L-valine, L-leucine and glycine, amino acids which are hydroxy-monoaminocarboxylic acids such as L-threonine and L-serine, cyclic amino acids such as L-proline, aromatic amino acids such as L-phenylalanine, L-tyrosine and L-tryptophan, sulfur-containing amino acids such as L-cysteine, L-cystine and L-methionine, and acidic amino acids such as L-glutamic acid, L-aspartic acid, L-glutamine and L-asparagine. Among these, L-lysine, L-arginine, L-histidine, L-isoleucine, L-valine, L-leucine, L-threonine, L-phenylalanine, L-tryptophan, L-cysteine and L-glutamic acid are preferred, and L-lysine, L-glutamic acid and L-threonine are particularly preferred.

<1-1> Imparting the Ability to Produce L-Amino Acids

Microorganisms belonging to the family Enterobacteriaceae can be used to derive the microorganisms which are able to produce L-amino acids, and typical examples are *Escherichia* and *Pantoea* bacteria. Other examples of microorganisms belonging to the family Enterobacteriaceae include γ-proteobacteria such as those of the genera *Enterobacter, Klebsiella, Serratia, Erwinia, Salmonella, Morganella*, or the like.

*Escherichia* bacteria described in Neidhardt et al. (Backmann B. J., 1996, Derivations and Genotypes of some mutant derivatives of *Escherichia coli* K-12, p. 2460-2488, Table 1: In F. D. Neidhardt (ed.), *Escherichia coli* and *Salmonella* Cellular and Molecular Biology/Second Edition, American Society for Microbiology Press, Washington, D.C.), such as *Escherichia coli*, can be utilized. Examples of wild-type strains of *Escherichia coli* include the K12 strain and derivatives thereof, *Escherichia coli* MG1655 strain (ATCC No. 47076), W3110 strain (ATCC No. 27325), and so forth. These strains can be obtained from, for example, the American Type Culture Collection (ATCC, Address: P.O. Box 1549, Manassas, Va. 20108, United States of America).

Examples of the *Enterobacter* bacteria include *Enterobacter agglomerans, Enterobacter aerogenes*, and so forth. An example of the *Pantoea* bacteria is *Pantoea ananatis*. In recent years, *Enterobacter agglomerans* is re-classified into *Pantoea agglomerans, Pantoea ananatis, Pantoea stewartii*, or the like based on the nucleotide sequence analysis of 16S rRNA, etc. The microorganism may be a bacterium which belongs to either the genus *Enterobacter* or *Pantoea*, so long as it is classified into the family Enterobacteriaceae. To breed a *Pantoea ananatis* strain by genetic engineering techniques, *Pantoea ananatis* AJ13355 strain (FERM BP-6614), AJ13356 strain (FERM BP-6615), AJ13601 strain (FERM BP-7207), derivatives thereof, and so forth can be used. These strains were identified as *Enterobacter agglomerans* when they were isolated, and deposited as *Enterobacter agglomerans*. However, they were recently re-classified as *Pantoea ananatis* based on the nucleotide sequence analysis of 16S rRNA, and so forth, as described above.

The methods for imparting an L-amino acid-producing ability to the bacterial strains as described above, or methods for enhancing an L-amino acid-producing ability of these strains, are described below.

Conventionally employed methods which are typically used in the breeding of bacteria of the genus *Escherichia* and so forth (see "Amino Acid Fermentation", Gakkai Shuppan Center (Ltd.), 1st Edition, published May 30, 1986, pp. 77-100) can be applied. Such methods include the acquisition of an auxotrophic strain, analogue-resistant strain, or a metabolic regulation mutant strain. Other commonly used methods include by constructing a recombinant strain which has increased expression of an L-amino acid biosynthetic enzyme. One or more properties, such as those described above, may be imparted to the chosen microorganism. The expression of one or more L-amino acid biosynthetic enzyme(s) can be enhanced in combination, or alone. Furthermore, the above-described properties such as auxotrophic mutation, analogue resistance, or metabolic regulation mutation, may be combined with the technique of enhancing the biosynthetic enzymes.

An auxotrophic mutant strain, L-amino acid analogue-resistant strain, or metabolic regulation mutant strain with the ability to produce an L-amino acid can be obtained by subjecting a parent strain or wild-type strain to conventional mutatagenesis, such as by exposure to X-rays or UV irradiation, or by treating with a mutagen such as N-methyl-N'-nitro-N-nitrosoguanidine, ethyl methanesulfonate (EMS), etc., then selecting the desired property and the ability to produce an L-amino acid.

Expression of a gene encoding an enzyme involved in the biosynthesis of the objective L-amino acid can be enhanced, reduction of the activity of a gene encoding an enzyme which acts to decompose the objective L-amino acid, and so forth, can be accomplished by genetic recomination.

Although specific examples of microorganisms having L-amino acid producing ability are mentioned below, the microorganisms are not limited to the following.

L-Threonine-Producing Bacteria

Examples of bacteria which can be used to derive L-threonine-producing bacteria include, but are not limited to, *Escherichia* strains, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631, 157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E.*

*coli* MG442 (Gusyatiner et al., Genetika (in Russian), 14, 947-956 (1978)), *E. coli* VL643 and VL2055 (EP 1149911 A), and so forth.

The TDH-6 strain is deficient in the thrC gene, as well as being sucrose-assimilative, and the ilvA gene has a leaky mutation. This strain also has a mutation in the rhtA gene, which imparts resistance to high concentrations of threonine or homoserine. The B-3996 strain contains the plasmid pVIC40 which was obtained by inserting the thrA*BC operon, which includes a mutant thrA gene, into the RSF100-derived vector. This mutant thrA gene encodes aspartokinase homoserine dehydrogenase I which is substantially desensitized to feedback inhibition by threonine. The B-3996 strain was deposited on Nov. 19, 1987 in the All-Union Scientific Center of Antibiotics (Nagatinskaya Street 3-A, 117105 Moscow, Russia) under the accession number RIA 1867. The strain was also deposited at the Russian National Collection of Industrial Microorganisms (VKPM) (1 Dorozhny proezd., 1 Moscow 117545, Russia) on Apr. 7, 1987 under the accession number VKPM B-3996.

*E. coli* VKPM B-5318 (EP 0593792 B) is also an L-threonine-producing bacterium. The B-5318 strain is prototrophic with regard to isoleucine, and a temperature-sensitive lambda-phage C1 repressor and PR promoter replace the regulatory region of the threonine operon in pVIC40. The VKPM B-5318 strain was deposited at the Russian National Collection of Industrial Microorganisms (VKPM) (1 Dorozhny proezd., 1 Moscow 117545, Russia) on May 3, 1990 under an accession number of VKPM B-5318.

Preferably, the bacterium is additionally modified to enhance expression of one or more of the following genes:

the mutant thrA gene which codes for aspartokinase-homoserine dehydrogenase I which is resistant to feedback inhibition by threonine;

the thrB gene which codes for homoserine kinase;

the thrC gene which codes for threonine synthase;

the rhtA gene which codes for a putative transmembrane protein;

the asd gene which codes for aspartate-β-semialdehyde dehydrogenase; and the aspC gene which codes for aspartate aminotransferase (aspartate transaminase).

The thrA gene which encodes aspartokinase-homoserine dehydrogenase I of *Escherichia coli* has been elucidated (nucleotide positions 337 to 2799, GenBank accession NC_000913.2, gi: 49175990), and is located between the thrL and thrB genes on the chromosome of *E. coli* K-12. The thrB gene which encodes homoserine kinase of *Escherichia coli* has been elucidated (nucleotide positions 2801 to 3733, GenBank accession NC_000913.2, gi: 49175990), and is located between the thrA and thrC genes on the chromosome of *E. coli* K-12. The thrC gene which encodes threonine synthase of *Escherichia coli* has been elucidated (nucleotide positions 3734 to 5020, GenBank accession NC_000913.2, gi: 49175990), and is located between the thrB gene and the yaaX open reading frame on the chromosome of *E. coli* K-12. All three genes function as a single threonine operon. To enhance expression of the threonine operon, the attenuator region which affects the transcription is desirably removed from the operon (WO2005/049808, WO2003/097839).

A mutant thrA gene which codes for aspartokinase-homoserine dehydrogenase I resistant to feedback inhibition by threonine, as well as the thrB and thrC genes, can be obtained as one operon from the well-known plasmid pVIC40, which is present in the threonine producing *E. coli* strain VKPM B-3996. pVIC40 is described in detail in U.S. Pat. No. 5,705,371.

The rhtA gene exists at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and is located between the pexB and ompX genes. This ORF1 region has been designated the rhtA gene (rht: resistance to homoserine and threonine). Also, it was revealed that the rhtA23 mutation is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession NC_000913.1, gi:16131307), and can be obtained by PCR (polymerase chain reaction; White, T. J. et al., Trends Genet., 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession NC_000913.1, gi:16128895), and can be obtained by PCR. The aspC genes from other microorganisms can be obtained in a similar manner.

L-Lysine-Producing Bacteria

Examples of L-lysine-producing *Escherichia* bacteria include mutants having resistance to an L-lysine analogue. The L-lysine analogue inhibits growth of *Escherichia* bacteria, but this inhibition is fully or partially desensitized when L-lysine is present in the culture medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutants that are resistant to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The WC196 strain is an L-lysine producing *Escherichia coli* bacterium. This bacterial strain was bred by conferring AEC resistance to the W3110 strain, which was derived from *Escherichia coli* K-12. The resulting strain was designated *Escherichia coli* AJ13069 and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received the accession number FERM BP-5252 (U.S. Pat. No. 5,827,698).

Examples of L-lysine-producing bacteria and parent strains which can be used to derive L-lysine-producing bacteria also include strains in which expression of one or more genes encoding an L-lysine biosynthetic enzyme are enhanced. Examples of such genes include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), and aspartase (aspA) (EP 1253195 A). In addition, the parent strains may have increased expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), the gene encoding glutamate dehydrogenase (gdhA, Gene, 23:199-209 (1983)), or combinations thereof. Abbreviations of the genes are indicated in the parentheses.

It is known that wild-type dihydrodipicolinate synthetase from *Escherichia coli* is subject to feedback inhibition by L-lysine, while wild-type aspartokinase from *Escherichia coli* is subject to suppression and feedback inhibition by L-lysine. Therefore, when the dapA and lysC genes are used, these genes have preferably been mutated so that they are not subject to feedback inhibition.

An example of a DNA encoding mutant dihydrodipicolinate synthetase desensitized to feedback inhibition by L-lysine includes a DNA encoding a protein which has the amino acid sequence in which the histidine at position 118 is replaced by tyrosine. Meanwhile, an example of a DNA encoding mutant aspartokinase desensitized to feedback inhibition by L-lysine includes a DNA encoding an AKIII having an amino acid sequence in which the threonine at position 352, the glycine at position 323, and the methionine at position 318 are replaced by isoleucine, asparagine, and isoleucine, respectively (U.S. Pat. No. 5,661,012 and U.S. Pat. No. 6,040,160). Such mutant DNAs can be obtained by a site-specific mutation using PCR or the like.

Wide host-range plasmids RSFD80, pCAB1, and pCABD2 are known to contain a mutant dapA gene encoding a mutant dihydrodipicolinate synthetase and a mutant lysC gene encoding a mutant aspartokinase (U.S. Pat. No. 6,040, 160). *Escherichia coli* JM109 strain transformed with RSFD80 was named AJ12396 (U.S. Pat. No. 6,040,160), and the strain was deposited at the National Institute of Bioscience and Human-Technology, Agency of Industrial Science and Technology, Ministry of International Trade and Industry (currently, International Patent Organism Depositary, National Institute of Advanced Industrial Science and Technology) on Oct. 28, 1993 and given an accession number of FERM P-13936, and the deposit was then converted to an international deposit under the provisions of Budapest Treaty on Nov. 1, 1994 and given an accession number of FERM BP-4859. RSFD80 can be obtained from the AJ12396 strain by a conventional method.

Examples of L-lysine-producing bacteria and parent strains for deriving L-lysine-producing bacteria also include strains with decreased or no activity of an enzyme that catalyzes a reaction which generates a compound other than L-lysine via a branch off of the biosynthetic pathway of L-lysine. Examples of these enzymes include homoserine dehydrogenase, lysine decarboxylase (U.S. Pat. No. 5,827, 698), and the malic enzyme (WO2005/010175). In order to reduce or delete the lysine decarboxylase activity, it is preferable to reduce expression of both the cadA and ldcC genes encoding lysine decarboxylase (International Patent Publication WO2006/038695).

L-Cysteine-Producing Bacteria

Examples of parent strains which can be used to derive L-cysteine-producing bacteria include, but are not limited to, *Escherichia* strains, such as *E. coli* JM15 which is transformed with different cysE alleles encoding feedback-resistant serine acetyltransferases (U.S. Pat. No. 6,218,168, Russian patent application 2003121601), *E. coli* W3110 with over-expressed genes which encode proteins which act to secrete substances which are toxic for cells (U.S. Pat. No. 5,972,663), *E. coli* strains having lowered cysteine desulfohydrase activity (JP11155571A2), and *E. coli* W3110 with increased activity of a positive transcriptional regulator for the cysteine regulon encoded by the cysB gene (WO0127307A1).

L-Leucine-Producing Bacteria

Examples of parent strains which can be used to derive L-leucine-producing bacteria include, but are not limited to, *Escherichia* strains, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine and 5,5,5-trifluoroleucine (JP 62-34397 B and JP 8-70879 A); *E. coli* strains obtained by the genetic engineering method described in WO96/06926; and *E. coli* H-9068 (JP 8-70879 A).

The bacterium may be improved by enhancing expression of one or more genes involved in L-leucine biosynthesis. Preferred examples of such genes include genes of the leuABCD operon, a typical example of which is the mutant leuA gene encoding isopropylmalate synthase which is not subject to feedback inhibition by L-leucine (U.S. Pat. No. 6,403,342). In addition, the bacterium may be improved by enhancing expression of one or more genes encoding proteins which excrete L-amino acid from the bacterial cell. Examples of such genes include b2682 and b2683 (ygaZH genes) (EP 1239041 A2).

L-Histidine-Producing Bacteria

Examples of parent strains which can be used to derive L-histidine-producing bacteria include, but are not limited to, *Escherichia* strains, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); and *E. coli* A180/pFM201 (U.S. Pat. No. 6,258,554).

Examples of parent strains which can be used to derive L-histidine-producing bacteria also include strains with enhanced expression of one or more genes encoding an L-histidine biosynthetic enzyme. Examples of such genes include genes encoding ATP phosphoribosyltransferase (hisG), phosphoribosyl AMP cyclohydrolase (hisI), phosphoribosyl-ATP pyrophosphohydrolase (hisIE), phosphoribosylformiminoamidotransferase (his H), histidinol phosphate aminotransferase (hisC), histidinol phosphatase (hisB), histidinol dehydrogenase (hisD), and so forth.

It is known that the L-histidine biosynthetic enzymes encoded by hisG and hisBHAF1 are inhibited by L-histidine, and therefore L-histidine-producing ability can also be efficiently enhanced by introducing a mutation which confers resistance to the feedback inhibition into the gene encoding ATP phosphoribosyltransferase (hisG) (Russian Patent Nos. 2003677 and 2119536).

Specific examples of strains having L-histidine-producing ability include *E. coli* FERM-P 5038 and 5048 which have been transformed with a vector carrying a DNA encoding an L-histidine-biosynthetic enzyme (JP 56-005099 A), *E. coli* strains transformed with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-Glutamic Acid-Producing Bacteria

Examples of parent strains which can be used to derive L-glutamic acid-producing bacteria include, but are not limited to, *Escherichia* strains, such as *E. coli* VL334thrC⁺ (EP 1172433). *E. coli* VL334 (VKPM B-1641) is auxotrophic for L-isoleucine and L-threonine and has mutations in the thrC and ilvA genes (U.S. Pat. No. 4,278,765). A wild-type allele of the thrC gene was transferred by general transduction using a bacteriophage P1 grown on the wild-type *E. coli* strain K12 (VKPM B-7) cells. As a result, an L-isoleucine auxotrophic strain VL334thrC⁺ (VKPM B-8961), which is able to produce L-glutamic acid, was obtained.

Examples of parent strains which can be used to derive the L-glutamic acid-producing bacteria include, but are not limited to, strains with enhanced expression of one or more genes encoding an L-glutamic acid biosynthetic enzyme. Examples of such genes include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), glucose phosphate isomerase (pgi), and so forth.

Examples of strains modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of parent strains which can be used to derive the L-glutamic acid-producing bacteria also include strains with decreased or no activity of an enzyme that catalyzes synthesis of a compound other than L-glutamic acid via a branch off of the L-glutamic acid biosynthesis pathway. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), glutamate decarboxylase (gadAB), and so forth. *Escherichia* bacteria deficient in α-ketoglutarate dehydrogenase activity or having reduced α-ketoglutarate dehydrogenase activity and methods for obtaining them are described in U.S. Pat. Nos. 5,378,616 and 5,573,945.

Specifically, these strains include the following:
*E. coli* W3110sucA::Kmʳ
*E. coli* AJ12624 (FERM BP-3853)
*E. coli* AJ12628 (FERM BP-3854)
*E. coli* AJ12949 (FERM BP-4881)

*E. coli* W3110sucA::Kmʳ is a strain obtained by disrupting the α-ketoglutarate dehydrogenase gene (hereinafter also referred to as "sucA gene") of *E. coli* W3110. This strain is completely deficient in α-ketoglutarate dehydrogenase.

Other examples of L-glutamic acid-producing bacterium include *Escherichia* bacteria which are resistant to an aspartic acid antimetabolite. These strains can also be deficient in α-ketoglutarate dehydrogenase activity and include, for example, *E. coli* AJ13199 (FERM BP-5807) (U.S. Pat. No. 5,908,768), AJ12624 (FFRM P-12379), which additionally is unable to, or to a very small extent, decompose L-glutamic acid (U.S. Pat. No. 5,393,671); AJ13138 (FERM BP-5565) (U.S. Pat. No. 6,110,714), and so forth.

Examples of L-glutamic acid-producing bacteria include mutant *Pantoea* strains which are deficient or have reduced α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6616. *Pantoea ananatis* AJ13356 is deficient in α-ketoglutarate dehydrogenase activity as a result of disruption of the αLKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, it is described as *Pantoea ananatis*.

L-Phenylalanine-Producing Bacteria

Examples of parent strains which can be used to derive L-phenylalanine-producing bacteria include, but are not limited to, *Escherichia* strains, such as *E. coli* AJ12739 (tyrA::Tn10, tyrR) (VKPM B-8197); *E. coli* HW1089 (ATCC 55371) harboring the mutant pheA34 gene (U.S. Pat. No. 5,354,672); *E. coli* MWEC101-b (KR8903681); and *E. coli* NRRL B-12141, NRRL B-12145, NRRL B-12146 and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ 12604 (FERM BP-3579) may be used (EP 488-424 B1). Furthermore, L-phenylalanine producing *Escherichia* bacteria with an enhanced activity of the protein encoded by the yedA gene or the yddG gene may also be used (U.S. patent applications 2003/0148473 A1 and 2003/0157667 A1).

L-Tryptophan-Producing Bacteria

Examples of parent strains which can be used to derive the L-tryptophan-producing bacteria include, but are not limited to, *Escherichia* strains, such as *E. coli* JP4735/pMU3028 (DSM10122) and JP6015/pMU91 (DSM10123) which are deficient in the tryptophanyl-tRNA synthetase encoded by a mutant trpS gene (U.S. Pat. No. 5,756,345); *E. coli* SV164 (pGH5) having a serA allele encoding phosphoglycerate dehydrogenase not subject to feedback inhibition by serine and a trpE allele encoding anthranilate synthase not subject to feedback inhibition by tryptophan (U.S. Pat. No. 6,180,373); *E. coli* AGX17 (pGX44) (NRRL B-12263) and AGX6 (pGX50)aroP (NRRL B-12264) deficient in the enzyme tryptophanase (U.S. Pat. No. 4,371,614); and *E. coli* AGX17/pGX50,pACKG4-pps in which a phosphoenolpyruvate-producing ability is enhanced (WO9708333, U.S. Pat. No. 6,319,696). L-tryptophan-producing *Escherichia* bacteria with enhanced activity of the protein encoded by and the yedA gene or the yddG gene may also be used (U.S. patent applications 2003/0148473 A1 and 2003/0157667 A1).

Examples of parent strains which can be used to derive the L-tryptophan-producing bacteria also include strains with enhanced activity of one or more enzymes, such as anthranilate synthase (trpE), phosphoglycerate dehydrogenase (serA), and tryptophan synthase (trpAB). The anthranilate synthase and phosphoglycerate dehydrogenase are both subject to feedback inhibition by L-tryptophan and L-serine, and therefore a mutation desensitizing the feedback inhibition may be introduced into these enzymes. Specific examples of strains having such a mutation include E. coli SV164 which harbors desensitized anthranilate synthase and a transformant strain obtained by introducing the pGH5 plasmid (WO94/08031), which contains a mutant serA gene encoding feedback inhibition-desensitized phosphoglycerate dehydrogenase, into the E. coli SV164.

Examples of parent strains which can be used to derive the L-tryptophan-producing bacteria also include strains which have the tryptophan operon which contains a gene encoding desensitized anthranilate synthase (JP 57-71397 A, JP 62-244382 A, U.S. Pat. No. 4,371,614). Moreover, L-tryptophan-producing ability may be imparted by enhancing expression of a gene which encodes tryptophan synthase in the tryptophan operon (trpBA). Tryptophan synthase includes α and β subunits which are encoded by the trpA and trpB genes, respectively. In addition, L-tryptophan-producing ability may also be improved by enhancing expression of the isocitrate lyase-malate synthase operon (WO2005/103275).

L-Tyrosine-Producing Bacteria

Examples of parent strains which can be used to derive L-tyrosine-producing bacteria include strains with enhanced activity of an aromatic amino acid biosynthesis system enzyme such as deoxyarabinoheptulonate-phosphate synthase (aroG), 3-dehydroquinate synthase (aroB), shikimate dehydrogenase (aroE), shikimate kinase (aroL), 5-enolpyruvate shikimate 3-phosphate synthase (aroA), and chorismate synthase (aroC) (EP 763127 A). It is also known that these genes are controlled by the tyrosine repressor (tyrR), and therefore, their activity may be enhanced by deleting the tyrR gene (European Patent No. 763127). The activities of these enzymes may also be enhanced in L-tryptophan-producing bacteria and L-phenylalanine-producing bacteria.

L-Proline-Producing Bacteria

Examples of parent strains which can be used to derive L-proline-producing bacteria include, but are not limited to, Escherichia strains, such as E. coli 702ilvA (VKPM B-8012) which is deficient in the ilvA gene and is able to produce L-proline (EP 1172433).

The bacterium may be improved by enhancing expression of one or more genes involved in L-proline biosynthesis. Examples of such genes include the proB gene encoding glutamate kinase desensitized to feedback inhibition by L-proline (DE Patent 3127361). In addition, the bacterium may be improved by enhancing expression of one or more genes encoding proteins responsible for secretion of L-amino acid from the bacterial cell. Such genes are exemplified by b2682 and b2683 (ygaZH genes) (EP1239041 A2).

Examples of Escherichia bacteria which have an activity to produce L-proline include the following E. coli strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15$^{th}$ Miami winter symposium, 1983, p. 34), and so forth.

L-Arginine-Producing Bacteria

Examples of parent strains which can be used to derive L-arginine-producing bacteria include, but are not limited to, Escherichia strains, such as E. coli strain 237 (VKPM B-7925) (U.S. Patent Application 2002/058315 A1) and its derivative strains harboring mutant N-acetylglutamate synthase (Russian Patent Application No. 2001112869), E. coli strain 382 (VKPM B-7926) (EP1170358A1), and an arginine-producing strain which has the argA gene encoding N-acetylglutamate synthetase (EP1170361A1).

Examples of parent strains which can be used to derive L-arginine-producing bacteria also include strains with enhanced expression of one or more genes encoding an L-arginine biosynthetic enzyme. Examples of such genes include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Valine-Producing Bacteria

Examples of parent strains which can be used to derive L-valine-producing bacteria include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by the produced L-valine. Furthermore, the ilvA gene in the operon is desirably disrupted so that threonine deaminase activity is decreased.

Examples of parent strains which can be used to derive L-valine-producing bacteria also include mutants of aminoacyl t-RNA synthetase (U.S. Pat. No. 5,658,766). For example, E. coli VL1970, which has a mutation in the ileS gene encoding isoleucine tRNA synthetase, can be used. E. coli VL1970 has been deposited in the Russian National Collection of Industrial Microorganisms (VKPM) (Russia, 117545 Moscow, 1 Dorozhny Proezd, 1) on Jun. 24, 1988 under accession number VKPM B-4411.

Furthermore, mutants requiring lipoic acid for growth and/or lacking H$^+$-ATPase can also be used as parent strains (WO96/06926).

L-Isoleucine-Producing Bacteria

Examples of parent strains which can be used to derive L-isoleucine producing bacteria include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

In order to enhance glycerol assimilability in bacteria, expression of the glpR gene (EP 1715056) may be attenuated, or expression of glycerol metabolism genes (EP 1715055 A) such as gipA, glpB, glpC, glpD, gipE, glpF, glpG, glpK, glpQ, gipT, glpX, tpiA, gldA, dhaK, dhaL, dhaM, dhaR, fsa, and talC genes may be enhanced.

<1-2> Enhancement of Activity

Orotate phosphoribosyltransferase (henceforth abbreviated as "OPRTase") activity is enhanced in a Enterobacteriaceae which has L-amino acid-producing ability as described, or the ability to produce an L-amino acid may be imparted after the OPRTase activity is enhanced.

The OPRTase activity can be enhanced by modifying the microorganism to increase the expression (amount of transcription) of the gene encoding OPRTase. The expression of the gene may be increased by modifying an expression control region, including modifying the promoter and so forth, of the endogenous gene, or by introducing an exogenous OPRTase gene on a plasmid and so forth. The OPRTase activity can also be increased by modifying the pyrE gene so that translation of OPRTase is increased. The OPRTase activity can also be increased by deleting the attenuator region of the pyrE gene, or by introducing a frameshift mutation into an upstream region of the OPRTase gene. The OPRTase activity can also be increased by modifying the pyrE gene so that the translation of OPRTase is increased. Any of these techniques may be combined.

The OPRTase activity means the generation of orotic acid and 5-phospho-α-D-ribose-monophosphate from orotidine-5'-phosphate and diphosphoric acid (refer to the following formula), and the enzyme is also called orotate phosphoribosyltransferase (EC 2.4.2.10).

Orotidine-5'-phosphate+diphosphoric acid→orotic acid+ 5-phospho-α-D-ribose-monophosphate Enhancement of the OPRTase activity can be confirmed by the method of Poulsen et al. (Eur. J. Biochem., 135:223-229, 1983).

The state of "being modified so that the OPRTase activity is enhanced" corresponds to when the number of OPRTase molecules per cell is increased as compared to that of the wild-type strain or unmodified strain, or when the activity of the OPRTase per molecule is improved as compared to that of the wild-type strain or unmodified strain. The OPRTase activity is improved by 150% or more, more preferably 200% or more, still more preferably 300% or more, per cell compared with the wild-type or unmodified strain. Examples of wild-type strains of Enterobacteriaceae, which can serve as a reference for comparison, include the *Escherichia coli* MG1655 (ATCC No. 47076) and W3110 strains (ATCC No. 27325), *Pantoea ananatis* AJ13335 strain (FERM BP-6615), and so forth.

The OPRTase activity can be enhanced by a modification that increases the expression of the gene encoding OPRTase. Increasing the expression as compared to a parent strain such as a wild-type or unmodified strain can be confirmed by comparing the amount of mRNA with that of the wild-type or unmodified strain. Examples of methods to measure expression include Northern hybridization and RT-PCR (Molecular Cloning, Cold Spring Harbor Laboratory Press, Cold spring Harbor (USA), 2001). Although the degree of the increase of the expression is not limited so long as it is increased as compared to the wild type or unmodified strain, it is desirably increased 1.5 times or more, more preferably 2 times or more, still more preferably 3 times or more, as compared to, for example, that of the wild-type or unmodified strain. Furthermore, he increased OPRTase activity can be confirmed by measuring the amount of OPRTase protein as compared to that of an unmodified or wild-type strain, and such increase can be detected by, for example, Western blotting using an antibody (Molecular Cloning, Cold spring Harbor Laboratory Press, Cold Spring Harbor (USA), 2001).

Examples of the gene encoding the protein having the OPRTase activity (pyrE gene) include, for example, the pyrE gene of *Escherichia coli*, specifically, the pyrE gene having the nucleotide sequence of numbers 782 to 1423 of SEQ ID NO: 11 (complementary strand of the nucleotide numbers 3813150 to 3813791 of GenBank Accession No. NC_00913 VERSION NC_000913.2 GI: 49175990).

Examples of the pyrE gene derived from other microorganisms include, for example, the pyrE gene of *Yersinia pestis* represented as a complementary strand of 577565.579529 of GenBank Accession No. NC_004088, the PYRE gene of *Salmonella typhi* represented as a complementary strand of 120832.122790 of GenBank Accession No. AL627282, the pyrE gene of *Bibrio cholerae* represented as a complementary strand of 305121.307121 of GenBank Accession No. NC_002505, the OPRTase gene of *Salmonella typhimurium* represented as a complementary strand of 4513714.4515672 of NC_003197, and so forth.

Furthermore, the pyrE gene may be a homologue of the pyrE gene which can be cloned from γ-proteobacteria of the genera *Escherichia*, *Enterobacter*, *Klebsiella*, *Serratia*, *Erwinia*, *Yersinia* and so forth, coryneform bacteria such as *Corynebacterium glutamicum* and *Brevibacterium lactofermentum*, *Pseudomonas* bacteria such as *Pseudomonas aeruginosa*, *Mycobacterium* bacteria such as *Mycobacterium tuberculosis*, and so forth, on the basis of homology to the genes exemplified above, and it may be a homologue which can be amplified by using, for example, the synthetic oligonucleotides shown in SEQ ID NOS: 9 and 10. Homology of amino acid sequences and nucleotide sequences can be determined using, for example, the algorithm BLAST of Karlin and Altschul (Pro. Natl. Acad. Sci. USA, 90, 5873 (1993)) or FASTA of Pearson (Methods Enzymol., 183, 63 (1990)). Programs called BLASTN and BLASTX have been developed on the basis of this algorithm BLAST (www.ncbi.nlm.nih.gov).

A homologue of the pyrE gene means a mutant gene derived from another microorganism or a natural or artificial mutant gene, which has high structural similarity to the aforementioned pyrE genes and is able to increase the OPRTase activity when it is introduced into a host or amplified in a host. The homologue of the pyrE gene means a gene encoding a protein having a homology of 80% or more, preferably 90% or more, more preferably 95% or more, particularly preferably 98% or more, to the entire amino acid sequence of SEQ ID NO: 12 and having the OPRTase activity. Whether or not a gene encodes a protein having OPRTase activity can be confirmed by expressing the gene in a host cell and measuring the OPRTase activity.

Furthermore, the pyrE gene is not limited to the wild-type gene, and it may be a mutant or artificially modified gene encoding a protein having the amino acid sequence of SEQ ID NO: 12, but which includes substitutions, deletions, insertions, additions or the like of one or more amino acid residues at one or more positions so long as the OPRTase activity of the encoded protein is not decreased.

Although the number of amino acid residues which may be changed depends on their positions in the three-dimensional structure or the types of amino acid residues, specifically, it may be preferably 1 to 20, more preferably 1 to 10, still more preferably 1 to 5. These substitutions are preferably conservative substitutions. The conservative mutation is wherein substitution takes place mutually among Phe, Trp and Tyr, if the substitution site is an aromatic amino acid; among Leu, Ile and Val, if it is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group. The examples of the conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. The aforementioned amino acid substitution, deletion, insertion, addition, inversion or the like may be the result of a naturally-occurring mutation or variation due to an individual difference or a difference of species of the microorganism (mutant or variant) having the OPRTase gene.

The pyrE gene may also be a DNA which is able to hybridize with a sequence complementary to the nucleotide sequence of SEQ ID NO: 12, or a probe that can be prepared from the nucleotide sequence, under stringent conditions and encodes a protein having the OPRTase activity. The "stringent conditions" referred to here are conditions under which a so-called specific hybrid is formed, and a non-specific hybrid is not formed, and specific examples include washing in typical Southern hybridization, i.e., washing once, preferably 2 or 3 times, at a salt concentration and temperature corresponding to 1×SSC, 0.1% SDS at 60° C., preferably 0.1×SSC, 0.1% SDS at 60° C., more preferably 0.1×SSC, 0.1% SDS at 68° C.

The modification which results in enhancing the expression of the aforementioned pyrE gene can be performed by increasing the copy number of the gene in the cells using, for example, a genetic recombination technique. For example, a DNA fragment containing the gene can be ligated to a vector which functions in a host microorganism, preferably a multicopy type vector, to prepare a recombinant DNA, and the recombinant DNA can then be introduced into the microorganism.

When the pyrE gene of *Escherichia coli* can be obtained by PCR (polymerase chain reaction, refer to White, T. J. et al., Trends Genet., 5, 185 (1989)) using primers prepared based on the nucleotide sequence of SEQ ID NO: 11, for example, the primers shown in SEQ ID NOS: 9 and 10, and the chromosomal DNA of *Escherichia coli* as the template. pyrE genes derived from other microorganisms can also be obtained from the chromosomal DNA or a chromosomal DNA library of each microorganism by PCR using oligonucleotides primers prepared based on the known OPRTase gene of the microorganism or the sequence information of the pyrE gene or pyrE protein from microorganisms of other species, or hybridization using an oligonucleotide probe prepared based on such sequence information as mentioned above. Chromosomal DNA can be prepared from a microorganism that serves as a DNA donor by the method of Saito and Miura (Saito H. and Miura K., 1963, Biochem. Biophys. Acta, 72, 619; Experiment Manual for Biotechnology, edited by The Society for Biotechnology, Japan, p 97-98, Baifukan Co., Ltd., 1992) or the like.

Then, the pyrE gene amplified by PCR is ligated to a vector DNA which can function in the cell of the host microorganism to prepare a recombinant DNA. Examples of the vector which can function in the cell of the host microorganism include vectors which are autonomously replicable in cells of the host microorganism.

Examples of vectors which are autonomously replicable in *Escherichia coli* include pUC19, pUC18, pHSG299, pHSG399, pHSG398, pACYC184, (pHSG and pACYC are available from Takara Bio Inc.), RSF1010 (Gene, vol. 75(2), p 271-288, 1989), pBR322, pMW219, pMW119 (pMW is available form Nippon Gene Co., Ltd.), pSTV28, and pSTV29 (Takara Bio Inc.). A phage DNA vector can also be used.

To ligate these genes to the above-mentioned vector, the vector is digested with a restriction enzyme corresponding to the termini of a DNA fragment containing the pyrE gene. Ligation is generally performed using a ligase such as T4 DNA ligase. Methods of digesting and ligating DNA, preparation of a chromosomal DNA, PCR, preparation of a plasmid DNA, transformation, design of oligonucleotides to be used as primers are methods well known to a person skilled in the art. These methods are described in Sambrook, J., Fritsch, E. F., and Maniatis, T., "Molecular Cloning A Laboratory Manual, Second Edition", Cold Sprig Harbor Laboratory Press, (1989), and so forth.

The resulting recombinant DNA may be introduced into a bacterium in accordance with a conventional transformation method, such as electroporation (Can. J. Microbiol., 43, 197 (1997)). It is also possible to increase the DNA permeability by treating recipient cells with calcium chloride, which has been reported with *Escherichia coli* K-12 (Mandel, M. and Higa, A., J. Mol. Biol., 53, 159 (1970), or to introduce DNA into a competent cell prepared from a cell at proliferation stage, which has been reported with *Bacillus subtilis* (Duncan, C. H., Wilson, G. A and Young, F. E, Gene, 1, 153 (1977)).

The copy number of the pyrE gene can also be increased by introducing multiple copies of the gene into the chromosomal DNA of the bacterium. Multiple copies of the gene can be introduced into the chromosomal DNA of the bacterium by homologous recombination using a target sequence which is present on the chromosomal DNA in multiple copies. This sequence may be a repetitive DNA or an inverted repeat which is present at the termini of a transposing element. Alternatively, as disclosed in JP 2-109985 A, multiple copies of the gene can be introduced into the chromosomal DNA by inserting the gene into a transposon, and transferring it so that multiple copies of the gene are integrated into the chromosomal DNA. Integration of these genes into the chromosome can be confirmed by Southern hybridization using a portion of the genes as a probe.

When a strain derived from *Escherichia coli* K12, for example, the MG1655 or W3110 strains, is used as the host, the ORPTase activity can also be increased by the following method. In *Escherichia coli*, the pyrE gene constitutes an operon with the rph gene, which is located upstream of the pyrE gene. The nucleotide sequence of the rph-pyrE operon of the *Escherichia coli* K12 strain is shown in SEQ ID NO: 11. In SEQ ID NO: 11, the coding region of the pyrE corresponds to the nucleotide numbers 782 to 1423. In the K12 strain, the coding region of rph contains a −1 frameshift mutation on the 3' end (between the 667th and 671st positions of SEQ ID NO: 11), resulting in a decrease in the translation of ORPTase and suppression of the activity (Journal of Bacteriology, vol. 175, June 1993, p 3401-3407). Therefore, in order to increase the activity of OPRTase, a mutation which counteracts the aforementioned −1 frameshift, for example, like a +1 or a −2 mutation, can be introduced into the region downstream of the 3' end of the rph gene and upstream of the pyrE gene. Specifically, for example, if one nucleotide is inserted into SEQ ID NO: 11 between the 670 and the 671 positions, the coding region of rph becomes longer, and the translation termination position of rph and the attenuator region which has high affinity to the ribosome becomes closer so that ribosome is unlikely to dissociate from the mRNA. As a result, the enzymatic activity of ORPTase is increased. The nucleotide sequence of the rph-pyrE operon with the pyrE gene upstream region in which the frameshift is suppressed is exemplified as SEQ ID NO: 13. In the sequence of SEQ ID NO: 13, the coding region of rph corresponds to the nucleotide numbers 1 to 714.

Moreover, if the region upstream of the attenuator is deleted and the aforementioned −1 frameshift is corrected via an insertion or deletion, the coding region of rph becomes longer, and the translation termination site of rph is closer to the translation initiation site of pyrE. Thus, the enzymatic activity of ORPTase is increased. Specifically, the ORPTase activity can be increased by deleting the nucleotide sequence of 610 to 691 of SEQ ID NO: 11. The resulting nucleotide sequence of the rph-pyrE operon is exemplified as SEQ ID NO: 14.

Furthermore, the expression of the pyrE gene may be enhanced by, besides increasing the copy number of the genes as described above, and as described in WO00/18935, an expression regulatory sequence such as the promoter can be substituted with a strong promoter, a regulator that increases expression of the gene can be amplified, or a regulator that decreases expression of the gene can be deleted or attenuated. Examples of known strong promoters include the lac promoter, trp promoter, trc promoter, tac promoter, lambda phage PR promoter, PL promoter, tet promoter, and so forth.

Methods for evaluating the potency of promoters and examples of strong promoters are described in the paper of Goldstein et al. (Prokaryotic promoters in biotechnology, Biotechnol. Annu. Rev., 1995, 1, 105-128), and so forth. Furthermore, it is known that by replacing several nucleotides in the spacer region between the ribosome binding site (RBS) and the start codon, particularly in the region immediately upstream from the start codon, the translation efficiency of mRNA can be significantly affected. These regions can also be modified. Expression of the OPRTase gene is enhanced by such substitution or modification of the promoter.

Furthermore, in order to enhance the activity of the protein encoded by the pyrE gene, a mutation that enhances the OPRTase activity may be introduced into these genes. Examples of a mutation that enhances the OPRTase activity include a mutation of the promoter sequence that increases the transcription of the pyrE gene, and a mutation in the coding region of the gene that increases the specific activity of the OPRTase protein.

<2> Method for Producing L-Amino Acid

The method for producing an L-amino acid includes by culturing the microorganism in a medium to produce and cause accumulation of an L-amino acid in the medium or cells, and collecting the L-amino acid from the medium or cells.

As the medium to be used, media which is conventionally used in the production of L-amino acids by fermentation using microorganisms can be used. That is, conventional media containing a carbon source, a nitrogen source, inorganic ions, and optionally other organic components as required may be used. As the carbon source, saccharides such as glucose, sucrose, lactose, galactose, fructose, and hydrolyzates of starches; alcohols such as glycerol and sorbitol; organic acids such as fumaric acid, citric acid and succinic acid and so forth can be used. As the nitrogen source, inorganic ammonium salts such as ammonium sulfate, ammonium chloride, and ammonium phosphate, organic nitrogen such as soybean hydrolysate, ammonia gas, aqueous ammonia, and so forth may be used. As for organic trace nutrient sources, it is desirable that the medium contains required substances such as vitamin B, and L-homoserine or yeast extract or the like in appropriate amounts. Other than the above, potassium phosphate, magnesium sulfate, iron ions, manganese ions, and so forth are added in small amounts, as required. In addition, the medium may be either a natural or synthetic medium, so long as it contains a carbon source, a nitrogen source, inorganic ions and other organic trace components as required.

Glycerol is a particularly preferable carbon source. Although the glycerol may be reagent-grade glycerol, it is desirable to use industrially produced glycerol which may contain impurities. For example, it is desirable to use glycerol industrially produced by the esterification reaction in biodiesel fuel production.

The glycerol in the medium may be the sole carbon source, or other carbon sources may also be added to the medium. Saccharides are preferred, such as glucose, fructose, sucrose, lactose, galactose, blackstrap molasses, and a sugar solution obtained by hydrolysis of starch hydrolysate or biomass, alcohols such as ethanol, and organic acids such as fumaric acid, citric acid, and succinic acid. When a mixed medium is used, it is desirable that glycerol is present in the medium at a ratio of 50% or more, preferably 60% or more, more preferably 70% or more, still more preferably 80% or more, especially preferably 90% or more. It is especially preferable to use glycerol obtained as a by-product of biodiesel fuel production (Mu Y, et al, Biotechnol Lett., 28, 1755-91759 (2006); Haas M. J., et al., Bioresour. Technol., 97, 4, 671-8678 (2006)).

The culture is preferably performed for 1 to 7 days under aerobic conditions. The culture temperature is preferably 24 to 45° C., and the pH during the culture is preferably 5 to 9. To adjust the pH, inorganic or organic acidic or alkaline substances, ammonia gas, and so forth can be used. The L-amino acid can be collected from the fermentation medium by a combination of known methods such as ion exchange and precipitation. When the L-amino acid accumulates in cells, the cells can be disrupted with, for example, supersonic waves or the like, and the L-amino acid can be collected by ion exchange or the like from the supernatant obtained by removing the cells from the cell-disrupted suspension by centrifugation.

When a basic amino acid is produced, the pH of the medium during the fermentation culture may be controlled to be 6.5 to 9.0, and the pH of the medium after completion of the culture may be controlled to be 7.2 to 9.0. The pressure in the fermentation tank during fermentation should be controlled so that it is positive, or carbon dioxide or a mixed gas containing carbon dioxide may be added to the medium so that bicarbonate ions and/or carbonate ions are present in an amount of at least 2 g/L in the culture medium. These bicarbonate ions and/or carbonate ions act as counter ions to the cations, mainly consisting of the basic amino acids, and the objective basic amino acid is then collected (Japanese Patent Laid-open No. 2002-065287, U.S. Published Patent Application No. 2002025564).

EXAMPLES

Hereinafter, the present invention will be still more specifically explained with reference to following non-limiting examples.

Example 1

Evaluation of a Glutamic Acid-Producing Strain which is Deficient in the Upstream Region of the pyrE Gene (1) Deletion of the sucA Gene of *Escherichia coli*

A sucA gene-deficient strain was prepared from the *Escherichia coli* MG1655 strain. Primers were synthesized based on the reported nucleotide sequence of the sucA gene, and used together with the genomic DNA of the MG1655 strain as the template to amplify the N- and C-terminus fragments of the sucA gene by PCR.

The primers 1 and 2 (SEQ ID NOS: 1 and 2) were used in PCR to amplify the N-terminus fragment, and the primers 3 and 4 (SEQ ID NOS: 3 and 4) were used in PCR to amplify the C-terminus fragment. Primer 1 was designed to contain a HindIII site, and primer 4 was designed to contain a XbaI site.

After PCR, the amplified DNA fragments were each purified by using the QIAquick PCR Purification Kit (QIAGEN). The purified N-terminal and C-terminal DNA fragments, and the primers 1 and 4 were used in crossover PCR (A. J. Link, D. Phillips, G. M. Church, Journal of Bacteriology, 179, 6228-6237 (1997)) to obtain a deletion-type sucA fragment. The purified DNA fragment was digested with HindIII and XbaI (Takara Shuzo) and subjected to a phenol/chloroform treatment and ethanol precipitation. This fragment was ligated with a temperature-sensitive plasmid pMAN997 (International Patent Publication WO99/03988) also digested with HindIII and XbaI using a DNA ligation Kit Ver. 2 (Takara Shuzo). JM109 competent cells (Takara Shuzo) were transformed with this ligation solution and applied to LB agar plates containing 25 μg/mL of ampicillin (Sigma) (LB+ampicillin plate). After the cells were cultured at 30° C. for one day, the colonies which appeared were cultured at 30° C. in LB medium containing 25 μg/mL of ampicillin in test tubes, and plasmids were extracted by using an automatic plasmid extractor PI-50 (Kurabo Industries). These plasmids were digested with HindIII and XbaI and subjected to agarose gel electrophoresis. The plasmid which contained the target fragment was designated as the pMAN_ΔsucA plasmid, denoting the sucA deletion. The aforementioned pMAN997 was obtained by exchanging VspI-HindIII fragments of pMAN031 (S. Matsuyama and S. Mizushima, J. Bacteriol., 162, 1196 (1985)) and pUC19 (Takara Shuzo).

The *E. coli* MG1655 strain was transformed with pMAN_ΔsucA according to the method of C. T. Chung et al. (Proc. Natl. Acad. Sci. U.S.A., 86, 2172 (1989)), and colonies were selected on an LB+ampicillin plate at 30° C. The selected clones were cultured overnight at 30° C. in a liquid culture, then the culture was diluted to $10^{-3}$ and plated on an LB+ampicillin plate, and colonies were selected at 42° C. The selected clones were applied to an LB+ampicillin plate and cultured at 30° C., and then ⅛ of the cells on the plate were suspended in 2 mL of LB medium and cultured at 42° C. for 4 to 5 hours with shaking. The culture was diluted to $10^{-5}$ and applied to an LB plate, and several hundreds of colonies among the obtained colonies were inoculated on LB plates and LB+ampicillin plates to confirm growth and thereby select ampicillin-sensitive strains. Colony PCR was performed for several ampicillin-sensitive strains to confirm the deletion of the sucA gene. Thus, a sucA-deficient strain derived from *E. coli* MG1655, MG1655ΔsucA, was obtained.

(2) Construction of a Strain in which the pyrE Upstream Region is Deleted (MG1655ΔsucA rph-pyrE(m)), from the sucA Gene-Deficient *Escherichia coli* Strain (MG1655ΔsucA)

The 82 bp sequence in the rph gene located upstream of the pyrE gene (5' end) on the chromosome of the MG1655ΔsucA strain (nucleotide sequence of *E. coli* MG1655 genome (coordinates 3813882 to 3813963 of GenBank ACCESSION: NC_000913, VERSION: NC_000913.2 GI: 49175990, nucleotide numbers 610 to 691 in SEQ ID NO: 11) can be deleted as follows. First, PCR is performed using MG1655 chromosomal DNA as the template and synthetic oligonucleotide primers 5 and 6 (SEQ ID NOS: 5 and 6) to obtain DNA fragment 1. PCR is similarly performed using synthetic oligonucleotide primers 7 and 8 (SEQ ID NOS: 7 and 8) to obtain DNA fragment 2. Then, PCR is performed using a mixture of DNA fragment 1 and DNA fragment 2 as the template and oligonucleotide primers 5 and 8 to obtain a deletion-type rph-pyrE fragment, and this fragment is inserted into the multi-cloning site of the temperature-sensitive plasmid pMAN997 (International Patent Publication WO99/03988) to obtain a plasmid for deletion, pMAN-rph-pyrE(m). The MG1655ΔsucA strain is transformed with this plasmid according to the method of C. T. Chung et al., and colonies are selected on an LB+ampicillin plate at 30° C. The selected clones are cultured overnight at 30° C. in a liquid culture, then the culture is diluted to $10^{-3}$ and plated on an LB+ampicillin plate, and colonies were selected at 42° C. The selected clones are applied to an LB+ampicillin plate and cultured at 30° C., and then ⅛ of the cells on the plate are suspended in 2 mL of LB medium and cultured at 42° C. for 4 to 5 hours with shaking. The culture is diluted to $10^{-5}$ and applied to an LB plate, and several hundreds of colonies among the obtained colonies are inoculated on an LB plate and LB+ampicillin plate to confirm growth and thereby select ampicillin-sensitive strains. Colony PCR is performed for several ampicillin-sensitive strains to confirm the deletion of the objective pyrE gene upstream region. Thus, a strain corresponding to a sucA-deleted strain MG1655ΔsucA derived from *E. coli* MG1655 in which the pyrE gene upstream region is deleted, MG1655ΔsucA rph-pyrE(m) strain, is obtained.

(3) Evaluation of the Ability to Produce Glutamic Acid of the MG1655ΔsucA rph-pyrE(m) Strain In order to examine the effect of the deletion of the pyrE gene upstream region on L-glutamic acid fermentation, the MG1655ΔsucAΔsucA rph-pyrE(m) strain and the control strain MG1655ΔsucA were cultured, and the produced L-glutamic acid was measured. The medium, culture method, and analysis method for the above are shown below. The L-glutamic acid yields observed after culture for 26.6 hours are shown in Table 1. The L-glutamic acid yields are indicated as averages for the two strains obtained by single colony isolation, each performed independently for two clones for each strain, totaling 4 strains.

MS Medium:
Final Concentrations:

| | |
|---|---|
| Glucose | 40 g/L (sterilized separately) |
| $MgSO_4 \cdot 7H_2O$ | 1 g/L (sterilized separately) |
| $(NH_4)_2SO_4$ | 16 g/L |
| $KH_2PO_4$ | 1 g/L |
| Yeast Extract | 2 g/L |
| $FeSO_4$ | 0.01 g/L |
| $MnSO_4$ | 0.01 g/L |
| $CaCO_3$ | 30 g/L (sterilized separately) |

Culture Method:
Refresh Culture:

The stored strain was inoculated on LB agar medium, and cultured at 37° C. for 24 hours.

Seed Culture in Test Tube:

The strain after the refresh culture was inoculated in LB liquid medium (drug was added as required), and cultured at 37° C. for 16 hours.

Main Culture:

The seed culture liquid medium was inoculated into 10% MS liquid medium (drug was added as required), and culture was performed at 37° C. in a volume of 20 ml in a 500 ml-volume Sakaguchi flask.

Analysis Method:

Glucose concentration and L-glutamic acid concentration were measured in a sample obtained by centrifuging the culture medium at 15,000 rpm for 5 minutes and diluting the supernatant with water at appropriate times with a Biotec Analyzer AS210 (SAKURA SEIKI). The glucose concentration in the medium after the culture for 26.6 hours was 11 g/L.

TABLE 1

Evaluation of glutamic acid-producing ability of
MG1655ΔsucA rph-pyrE(m) strain

| | Glutamic acid yield (%) |
|---|---|
| MG1655ΔsucA | 36.9 |
| MG1655ΔsucA rph-pyrE(m) | 40.9 |

Example 2

Evaluation of the pyrE Gene-Amplified Threonine-Producing Strain (1) Construction of pyrE-Amplified Strains from *Escherichia coli* Threonine-Producing Strains B-3996 and B-5318

The plasmid for pyrE amplification was constructed as follows. PCR was performed using the MG1655 chromosomal DNA as the template and synthetic oligonucleotide primers 9 and 10 (SEQ ID NOS: 9 and 10) to obtain a pyrE gene fragment. This was cloned into the plasmid vectors pMW219 (Nippon Gene) and pSTV28 (TaKaRa) at the SmaI site to obtain pMW219-pyrE and pSTV28-pyrE, respectively.

PyrE-gene amplified strains of the threonine-producing strains B-3996 and B-5318 strains can be obtained by introducing pMW219-pyrE and pSTV28-pyrE into the B-3996 strain and B-5318 strain by electroporation.

(2) Evaluation of L-Threonine-Producing Ability of *Escherichia coli* Threonine-Producing Strain B-3996 and pyrE Gene-Amplified B-3996 Strain The B-3996 strain and the pyrE-amplified strain derived from B-3996 can be cultured as follows, and then the amount of L-threonine in the media can be measured to demonstrate that the pyrE-amplified strain produces a higher threonine yield compared with the non-amplified control strain.

Medium:

Glucose: 40.0 g/l (A), $K_2HPO_4$: 0.7 g/l (B), thiamine HCl: 0.2 mg/l (C), $MgSO_4 \cdot 7H_2O$: 1.0 g/l (D), $(NH_4)_2SO_4$: 16.0 g/l (D), $FeSO_4 \cdot 7H_2O$: 0.01 g/l (D), $MnSO_4 \cdot 5H_2O$: 0.01 g/l, yeast extract: 2.0 g/l (D), L-isoleucine: 0.05 g/l (D)

The components of A, B, and D are each adjusted to pH 7.0 with KOH, separately sterilized (115° C., 10 minutes in autoclave) and then mixed, and the component of (C) is added to the mixture after filture sterilization.

Culture Method:

LB medium in which each of the aforementioned strains is cultured overnight is inoculated into 1 ml to 20 ml of the aforementioned medium, and culture is performed at 37° C. in a 500-ml Sakaguchi flask with shaking.

Analysis Method:

The culture is centrifuged at 15,000 rpm for 5 minutes, the supernatant is diluted at appropriate times with water, and analysis is performed with the amino acid analyzer L-8500.

Example 3

Evaluation of pyrE Gene-Amplified L-Glutamic Acid-Producing Strain

The *Pantoea ananatis* AJ13601 strain can be used to derive the L-glutamic acid producing strain with increased OPRTase activity. The *Pantoea ananatis* AJ13601 strain was deposited at the National Institute of Bioscience and Human-Technology, Agency of Industrial Science and Technology, Ministry of Economy, Trade and Industry (Tsukuba Central 6, 1-1, Higashi 1-Chome, Tsukuba-shi, Ibaraki-ken, Japan, postal code: 305-8566, currently National Institute of Advanced Industrial Science and Technology, International Patent Organism Depositary) on Aug. 18, 1999, and assigned an accession number FERM P-17516. Then, the deposit was converted into an international deposit under the provisions of the Budapest Treaty on Jul. 6, 2000, and assigned an accession number FERM BP-7207. A pyrE gene-amplified strain of an L-glutamic acid-producing bacterium can be obtained by introducing pMW219-pyrE or pSTV28-pyrE in the same manner as that in Example 2.

A pyrE gene-amplified strain is cultured in an L-glutamic acid production medium using a reciprocally shaking culture machine. After the culture, the amount of L-glutamic acid which is present in the medium is measured by a known method to confirm the increased of L-glutamic acid production. The pyrE gene-amplified strain showing the improved L-glutamic acid-producing ability can be obtained by such a method.

Example 4

Construction of OPRTase Activity-Enhanced L-Lysine-Producing Strain

<1> Construction of OPRTase Activity-Improved Strain

The OPRTase activity of the *Escherichia coli* WC196ΔcadAΔldc strain described in International Patent Publication WO2006/078039 was enhanced. This strain corresponds to the *Escherichia coli* WC1-96 strain in which the lysine decarboxylase genes cadA and ldc are disrupted by a combination of Red-driven integration (Datsenko, K. A. and Wanner B. L., 2000, Proc. Natl. Acad. Sci. USA. 97:6640-6645) and using the excisive system derived from λ phage (Cho E. H., Gumport R. I., and Gardner J. F., J. Bacteriol., 184:5200-5203 (2002)) (WO2005/010175).

The sequence upstream of the pyrE gene on the chromosome of the WC196ΔcadAΔldc strain was modified so that this gene is controlled by the tacM1 promoter. The nucleotide sequence of the modified pyrE gene is shown in SEQ ID NO: 16. The nucleotide numbers 1741 to 2382 of SEQ ID NO: 16 correspond to the pyrE coding region. Expression of the modified pyrE gene is not controlled by any attenuator, and translation of the transcript into OPRTase is also not affected by the frameshift mutation of the rph gene.

The nucleotide sequence shown in SEQ ID NO: 15 was used for the aforementioned modification of the pyrE gene. In the nucleotide sequence shown in SEQ ID NO: 15, the nucleotide numbers 1 to 172 correspond to the attR sequence of λ phage, the nucleotide numbers 324 to 983 correspond to the chloramphenicol resistance gene (cat), the nucleotide numbers 1540 to 1653 correspond to the attL sequence of λ phage and the nucleotide numbers 1654 to 1733 correspond to the tacM1 promoter, and the remainder corresponds to the sequence derived from pMW118. The tacM1 promoter can be constructed by replacing the TTGACA sequence in the −35 region of the tac promoter (Gene, 25 (2-3), 167-178 (1983)) with TTGGCA (nucleotide numbers 1669 to 1674 of SEQ ID NO: 15). The sequence of SEQ ID NO: 16 can be constructed by referring to pMW118-attL-Cm-attR described in WO2005/010175.

A DNA fragment having the sequence of SEQ ID NO: 15 was amplified as the template by PCR using primers having the nucleotide sequences shown in SEQ ID NOS: 17 and 18. This amplification product was inserted into the chromosome of the WC196ΔcadAΔldc strain by the λ-RED method (WO2005/010175) to obtain a strain with a modified promoter sequence upstream of pyrE. The WC196ΔAcadAΔldcCPtacM1pyrE::Cm strain, in which the activity of orotate phosphoribosyltransferase was increased, was thereby obtained.

<2> Construction of OPRTase Activity-Enhanced L-Lysine-Producing Bacterium

The WC196ΔcadAΔldcC strain and the WC196ΔcadAΔldcCPtacM1pyrE::Cm strain were transformed with the pCABD2 plasmid carrying the dapA, dapB and lysC genes (International Patent Publication WO01/53459) in a conventional manner to obtain WC196ΔcadAΔldcC/pCABD2 and WC196ΔcadAΔldcCPtacM1pyrE::Cm/pCABD2 strains.

These strains were each cultured at 37° C. in L medium containing 20 mg/L of streptomycin until OD600 became about 0.6, then the culture was added with an equal volume of 40% glycerol solution, and the mixture was stirred, divided into appropriate volumes, and stored at −80° C. These mixtures are glycerol stocks.

Example 5

Evaluation of OPRTase Activity-Enhanced L-Lysine-Producing Bacterium

The aforementioned glycerol stocks were thawed, and uniformly applied to an L plate containing 20 mg/L of streptomycin in a volume of 100 μL each, and culture was performed at 37° C. for 24 hours. About ⅛ of the obtained cells on one plate were inoculated into 20 mL of fermentation medium containing 20 mg/L of streptomycin in a 500-mL Sakaguchi flask, and cultured at 37° C. for 24 hours on a reciprocally shaking culture machine. After the culture, the amount of L-lysine present in the medium was measured by a known method (Biotec Analyzer AS210, SAKURA SEIKI). The composition of the fermentation medium is shown below.

Composition of Fermentation Medium:

| | |
|---|---|
| Glycerol or glucose | 40 g/L |
| $(NH_4)_2SO_4$ | 24 g/L |
| $KH_2PO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 5H_2O$ | 0.01 g/L |
| Yeast Extract | 2.0 g/L |

The medium was adjusted to pH 7.0 with KOH, autoclaved at 115° C. for 10 minutes (provided that glycerol or glucose and $MgSO_4 \cdot 7H_2O$ were separately sterilized) and then 30 g/L of $CaCO_3$ defined in Japanese Pharmacopoeia (subjected to hot air sterilization at 180° C. for 2 hours) was added.

20 mg/L of streptomycin was added to the aforementioned medium. Culture was performed at a temperature of 37° C. and stirred at 115 rpm for 24 hours.

The results are shown in Table 2 (O.D. represents the cell amount and was measured at 660 nm for the medium diluted 26 times, and Lys (g/L) represents the amount of L-lysine present in the flask). For both cases, glycerol and glucose were the carbon source, and the OPRTase activity-enhanced strain produced a larger amount of L-lysine compared with the unmodified control strain.

TABLE 2

| | | O.D. | Lys (g/L) |
|---|---|---|---|
| Glycerol | | | |
| WC196LC | pCABD2 | 0.31 | 3.1 |
| WC196LCPtacM1pyrE | pCABD2 | 0.36 | 3.8 |
| Glucose | | | |
| WC196LC | pCABD2 | 0.33 | 6.8 |
| WC196LCPtacM1pyrE | pCABD2 | 0.42 | 8.1 |

INDUSTRIAL APPLICABILITY

By using the microorganism of the present invention, basic amino acids such as L-lysine, L-ornithine, L-arginine, L-histidine and L-citrulline, aliphatic amino acids such as L-isoleucine, L-alanine, L-valine, L-leucine and glycine, amino acids which are hydroxy-monoaminocarboxylic acids such as L-threonine and L-serine, cyclic amino acids such as L-proline, aromatic amino acids such as L-phenylalanine, L-tyrosine and L-tryptophan, sulfur-containing amino acids such as L-cysteine, L-cystine and L-methionine, and acidic amino acids such as L-glutamic acid, L-aspartic acid, L-glutamine and L-asparagine can be efficiently produced by fermentation.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing an L-amino acid, wherein the L-amino acid is selected from the group consisting of L-lysine, L-arginine, L-histidine, L-isoleucine, L-valine, L-leucine, L-threonine, L-phenylalanine, L-tyrosine, L-tryptophan, L-cysteine, L-glutamic acid, and combinations thereof, which comprises:
   A) culturing a microorganism in a medium, and
   B) collecting the L-amino acid from the medium or the microorganism, wherein the microorganism belongs to the family Enterobacteriaceae and is able to produce an L-amino acid, and wherein the microorganism has been modified to enhance orotate phosphoribosyltransferase activity.

2. The method according to claim 1, wherein glycerol is present in the medium as the carbon source.

3. The method according to claim 1, wherein the orotate phosphoribosyltransferase activity is enhanced by a method selected from the group consisting of:
   A) increasing the expression of the pyrE gene which encodes orotate phosphoribosyltransferase,
   B) increasing the translation of orotate phosphoribosyltransferase, and
   C) combinations thereof.

4. The method according to claim 1, wherein the orotate phosphoribosyltransferase activity is enhanced by a method selected from the group consisting of:
   A) increasing the copy number of the pyrE gene which encodes orotate phosphoribosyltransferase,
   B) modifying an expression control sequence of the pyre gene, and
   C) combinations thereof.

5. The method according to claim 1, wherein the rph-pyrE operon is modified in the microorganism, and wherein the orotate phosphoribosyltransferase activity is enhanced by the introduction of a mutation which complements a native −1 frameshift mutation in the coding region of the rph gene.

6. The method according to claim 1, wherein the orotate phosphoribosyltransferase activity is enhanced by the deletion of the attenuator located upstream of the pyrE gene.

7. The method according to claim 3, wherein the orotate phosphoribosyltransferase is selected from the group consisting of:
   (A) a protein comprising the amino acid sequence of SEQ ID NO: 12,
   (B) a protein comprising the amino acid sequence of SEQ ID NO: 12 but which includes substitutions, deletions, insertions, additions or inversions of one to 5 amino acid residues, and has orotate phosphoribosyltransferase activity.

8. The method according to claim 3, wherein the pyrE gene is selected from the group consisting of:
   (a) a DNA comprising the nucleotide sequence of number 782 to 1423 of SEQ ID NO: 11, and
   (b) a DNA which is able to hybridize with a nucleotide sequence complementary to the nucleotide sequence of numbers 782 to 1523 of SEQ ID NO: 11 under stringent conditions comprising washing with 0.1×SSC and 0.1% SDS, at 60° C., and encoding a protein having orotate phosphoribosyltransferase activity.

9. The method according to claim 1, wherein the microorganism belongs to a genera selected from the group consisting of *Escherichia, Enterobacter*, and *Pantoea*.

10. The method according to claim 1, wherein the microorganism is *Escherichia coli* or *Pantoea ananatis*.

* * * * *

SEQUENCE LISTING

<160> NUMBER OF SEQ ID NOS: 18

<210> SEQ ID NO 1
<211> LENGTH: 29
<212> TYPE: DNA
<213> ORGANISM: Artificial
<220> FEATURE:
<223> OTHER INFORMATION: primer

<400> SEQUENCE: 1
cccaagcttc tgcccctgac actaagaca                29

<210> SEQ ID NO 2

```
<211> LENGTH: 20
<212> TYPE: DNA
<213> ORGANISM: Artificial
<220> FEATURE:
<223> OTHER INFORMATION: primer

<400> SEQUENCE: 2
cgaggtaacg ttcaagacct                                                   20

<210> SEQ ID NO 3
<211> LENGTH: 40
<212> TYPE: DNA
<213> ORGANISM: Artificial
<220> FEATURE:
<223> OTHER INFORMATION: primer

<400> SEQUENCE: 3
aggtcttgaa cgttacctcg atccataacg ggcagggcgc                             40

<210> SEQ ID NO 4
<211> LENGTH: 29
<212> TYPE: DNA
<213> ORGANISM: Artificial
<220> FEATURE:
<223> OTHER INFORMATION: primer

<400> SEQUENCE: 4
gggtctagac cactttgtca gtttcgatt                                         29

<210> SEQ ID NO 5
<211> LENGTH: 25
<212> TYPE: DNA
<213> ORGANISM: Artificial
<220> FEATURE:
<223> OTHER INFORMATION: primer

<400> SEQUENCE: 5
ccgccatttc cggcttctct tccag                                             25

<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
gcagaaggcg gcgctggcaa a                                                 21

<210> SEQ ID NO 7
<211> LENGTH: 23
<212> TYPE: DNA
<213> ORGANISM: Artificial
<220> FEATURE:
<223> OTHER INFORMATION: primer

<400> SEQUENCE: 7
gtcccctgca cttcaatgat gcg                                               23

<210> SEQ ID NO 8
<211> LENGTH: 25
<212> TYPE: DNA
<213> ORGANISM: Artificial
<220> FEATURE:
<223> OTHER INFORMATION: primer

<400> SEQUENCE: 8
```
ttgtttcaag ccggagattt caata                                    25

<210> SEQ ID NO 9
<211> LENGTH: 25
<212> TYPE: DNA
<213> ORGANISM: Artificial
<220> FEATURE:
<223> OTHER INFORMATION: primer

<400> SEQUENCE: 9
gaagacgggc gcatcattga agtgc                                    25

<210> SEQ ID NO 10
<211> LENGTH: 25
<212> TYPE: DNA
<213> ORGANISM: Artificial
<220> FEATURE:
<223> OTHER INFORMATION: primer

<400> SEQUENCE: 10
cggcacagtt gcagtaatat gacgc                                    25

<210> SEQ ID NO 11
<211> LENGTH: 1423
<212> TYPE: DNA
<213> ORGANISM: Escherichia coli
<220> FEATURE:
<221> NAME/KEY: CDS
<222> LOCATION: (782)..(1423)

<400> SEQUENCE: 11
atgcgtccag caggccgtag caataatcag gtgcgtcccg ttaccctgac tcgtaactat    60
acaaaacatg cagaaggctc ggtgctggtc gaatttggcg ataccaaagt gttgtgtacc   120
gcctctattg aagaaggcgt gccgcgcttc ctgaaaggtc agggccaggg ctggatcacc   180
gcagagtacg gcatgctgcc acgttctacc cacacccgta acgctcgtga agcggcgaaa   240
ggtaagcagg gtggacgcac aatggaaatc agcgtctga tcgcccgtgc tcttcgcgcg   300
gcagtagatt tgaaagcgct gggtgagttc accattacgc tggactgcga cgtgcttcag   360
gctgatggtg gcacgcgtac cgcgtcgatt acgggtgcct gcgtggcgct ggtagatgcg   420
ctacagaagc tggtggaaaa cggcaagctg aaaaccaatc cgatgaaagg gatggtagcc   480
gcagtttctg tcggaattgt gaacggcgaa gcggtttgcg atctggaata cgttgaagac   540
tctgccgcag agaccgacat gaacgtagtg atgaccgaag acgggcgcat cattgaagtg   600
caggggacgg cagaaggcga gccgttcacc catgaagagc tactcatctt gttggctctg   660
gcccgagggg aatcgaatcc attgtagcga cgcagaaggc ggcgctggca aactgatttt   720
taaggcgact gatgagtcgc cttttttttg tctgtagaaa agtaagatga ggagcgaagg   780 c atg aaa cca tat cag cgc cag ttt att gaa ttt gcg ctt agc aag cag    829
  Met Lys Pro Tyr Gln Arg Gln Phe Ile Glu Phe Ala Leu Ser Lys Gln
  1               5                  10                  15 gtg tta aag ttt ggc gag ttt acg ctg aaa tcc ggg cgc aaa agc ccc      877
Val Leu Lys Phe Gly Glu Phe Thr Leu Lys Ser Gly Arg Lys Ser Pro
             20                  25                  30 tat ttc ttc aac gcc ggg ctg ttt aat acc ggg cgc gat ctg gca ctg      925
Tyr Phe Phe Asn Ala Gly Leu Phe Asn Thr Gly Arg Asp Leu Ala Leu
         35                  40                  45 tta ggc cgt ttt tac gct gaa gcg ttg gtg gat tcc ggc att gag ttc      973
Leu Gly Arg Phe Tyr Ala Glu Ala Leu Val Asp Ser Gly Ile Glu Phe
     50                  55                  60 gat ctg ctg ttt ggc cct gct tac aaa ggg atc ccg att gcc acc aca     1021

```
Asp Leu Leu Phe Gly Pro Ala Tyr Lys Gly Ile Pro Ile Ala Thr Thr
 65                  70                  75                  80 acc gct gtg gca ctg gcg gag cat cac gac ctg gac ctg ccg tac tgc      1069
Thr Ala Val Ala Leu Ala Glu His His Asp Leu Asp Leu Pro Tyr Cys
                     85                  90                  95 ttt aac cgc aaa gaa gca aaa gac cac ggt gaa ggc ggc aat ctg gtt      1117
Phe Asn Arg Lys Glu Ala Lys Asp His Gly Glu Gly Gly Asn Leu Val
                100                 105                 110 ggt agc gcg tta caa gga cgc gta atg ctg gta gat gat gtg atc acc      1165
Gly Ser Ala Leu Gln Gly Arg Val Met Leu Val Asp Asp Val Ile Thr
            115                 120                 125 gcc gga acg gcg att cgc gag tcg atg gag att att cag gcc aat ggc      1213
Ala Gly Thr Ala Ile Arg Glu Ser Met Glu Ile Ile Gln Ala Asn Gly
        130                 135                 140 gcg acg ctt gct ggc gtg ttg att tcg ctc gat cgt cag gaa cgc ggg      1261
Ala Thr Leu Ala Gly Val Leu Ile Ser Leu Asp Arg Gln Glu Arg Gly
145                 150                 155                 160 cgc ggc gag att tcg gcg att cag gaa gtt gag cgt gat tac aac tgc      1309
Arg Gly Glu Ile Ser Ala Ile Gln Glu Val Glu Arg Asp Tyr Asn Cys
                165                 170                 175 aaa gtg atc tct atc atc acc ctg aaa gac ctg att gct tac ctg gaa      1357
Lys Val Ile Ser Ile Ile Thr Leu Lys Asp Leu Ile Ala Tyr Leu Glu
            180                 185                 190 gag aag ccg gaa atg gcg gaa cat ctg gcg gcg gtt aag gcc tat cgc      1405
Glu Lys Pro Glu Met Ala Glu His Leu Ala Ala Val Lys Ala Tyr Arg
        195                 200                 205 gaa gag ttt ggc gtt taa                                              1423
Glu Glu Phe Gly Val
            210

<210> SEQ ID NO 12
<211> LENGTH: 213
<212> TYPE: PRT
<213> ORGANISM: Escherichia coli

<400> SEQUENCE: 12

Met Lys Pro Tyr Gln Arg Gln Phe Ile Glu Phe Ala Leu Ser Lys Gln
 1               5                  10                  15

Val Leu Lys Phe Gly Glu Phe Thr Leu Lys Ser Gly Arg Lys Ser Pro
                20                  25                  30

Tyr Phe Phe Asn Ala Gly Leu Phe Asn Thr Gly Arg Asp Leu Ala Leu
            35                  40                  45

Leu Gly Arg Phe Tyr Ala Glu Ala Leu Val Asp Ser Gly Ile Glu Phe
    50                  55                  60

Asp Leu Leu Phe Gly Pro Ala Tyr Lys Gly Ile Pro Ile Ala Thr Thr
 65                  70                  75                  80

Thr Ala Val Ala Leu Ala Glu His His Asp Leu Asp Leu Pro Tyr Cys
                     85                  90                  95

Phe Asn Arg Lys Glu Ala Lys Asp His Gly Glu Gly Gly Asn Leu Val
                100                 105                 110

Gly Ser Ala Leu Gln Gly Arg Val Met Leu Val Asp Asp Val Ile Thr
            115                 120                 125

Ala Gly Thr Ala Ile Arg Glu Ser Met Glu Ile Ile Gln Ala Asn Gly
        130                 135                 140

Ala Thr Leu Ala Gly Val Leu Ile Ser Leu Asp Arg Gln Glu Arg Gly
145                 150                 155                 160

Arg Gly Glu Ile Ser Ala Ile Gln Glu Val Glu Arg Asp Tyr Asn Cys
                165                 170                 175
```

-continued

Lys Val Ile Ser Ile Ile Thr Leu Lys Asp Leu Ile Ala Tyr Leu Glu
                180                 185                 190

Glu Lys Pro Glu Met Ala Glu His Leu Ala Ala Val Lys Ala Tyr Arg
        195                 200                 205

Glu Glu Phe Gly Val
        210

<210> SEQ ID NO 13
<211> LENGTH: 1424
<212> TYPE: DNA
<213> ORGANISM: Artificial
<220> FEATURE:
<223> OTHER INFORMATION: artificially modified rph-pyrE operon

<400> SEQUENCE: 13

| | | | | | | |
|---|---|---|---|---|---|---|
| atgcgtccag | caggccgtag | caataatcag | gtgcgtcccg | ttaccctgac | tcgtaactat | 60 |
| acaaaacatg | cagaaggctc | ggtgctggtc | gaatttggcg | ataccaaagt | gttgtgtacc | 120 |
| gcctctattg | aagaaggcgt | gccgcgcttc | ctgaaaggtc | agggccaggg | ctggatcacc | 180 |
| gcagagtacg | gcatgctgcc | acgttctacc | cacacccgta | acgctcgtga | agcggcgaaa | 240 |
| ggtaagcagg | tggacgcac | aatggaaatc | cagcgtctga | tcgcccgtgc | tcttcgcgcg | 300 |
| gcagtagatt | tgaaagcgct | gggtgagttc | accattacgc | tggactgcga | cgtgcttcag | 360 |
| gctgatggtg | gcacgcgtac | cgcgtcgatt | acgggtgcct | gcgtggcgct | ggtagatgcg | 420 |
| ctacagaagc | tggtggaaaa | cggcaagctg | aaaaccaatc | gatgaaagg | gatggtagcc | 480 |
| gcagtttctg | tcggaattgt | gaacggcgaa | gcggtttgcg | atctggaata | cgttgaagac | 540 |
| tctgccgcag | agaccgacat | gaacgtagtg | atgaccgaag | acgggcgcat | cattgaagtg | 600 |
| caggggacgg | cagaaggcga | gccgttcacc | catgaagagc | tactcatctt | gttggctctg | 660 |
| gccccgaggg | gaatcgaatc | cattgtagcg | acgcagaagg | cggcgctggc | aaactgattt | 720 |
| ttaaggcgac | tgatgagtcg | cctttttttt | gtctgtagaa | aagtaagatg | aggagcgaag | 780 |
| gcatgaaacc | atatcagcgc | cagtttattg | aatttgcgct | tagcaagcag | gtgttaaagt | 840 |
| ttggcgagtt | tacgctgaaa | tccgggcgca | aaagcccta | tttcttcaac | gccgggctgt | 900 |
| taataccgg | gcgcgatctg | gcactgttag | gccgttttta | cgctgaagcg | ttggtggatt | 960 |
| ccggcattga | gttcgatctg | ctgtttggcc | ctgcttacaa | agggatcccg | attgccacca | 1020 |
| caaccgctgt | ggcactggcg | gagcatcacg | acctggacct | gccgtactgc | tttaaccgca | 1080 |
| aagaagcaaa | agaccacggt | gaaggcggca | atctggttgg | tagcgcgtta | caaggacgcg | 1140 |
| taatgctggt | agatgatgtg | atcaccgccg | gaacggcgat | tcgcgagtcg | atggagatta | 1200 |
| ttcaggccaa | tggcgcgacg | cttgctggcg | tgttgatttc | gctcgatcgt | caggaacgcg | 1260 |
| ggcgcggcga | gatttcggcg | attcaggaag | ttgagcgtga | ttacaactgc | aaagtgatct | 1320 |
| ctatcatcac | cctgaaagac | ctgattgctt | acctggaaga | gaagccggaa | atggcggaac | 1380 |
| atctggcggc | ggttaaggcc | tatcgcgaag | agtttggcgt | ttaa | | 1424 |

<210> SEQ ID NO 14
<211> LENGTH: 1341
<212> TYPE: DNA
<213> ORGANISM: Artificial
<220> FEATURE:
<223> OTHER INFORMATION: artificially modified rph-pyrE operon

<400> SEQUENCE: 14

| | | | | | | |
|---|---|---|---|---|---|---|
| atgcgtccag | caggccgtag | caataatcag | gtgcgtcccg | ttaccctgac | tcgtaactat | 60 |
| acaaaacatg | cagaaggctc | ggtgctggtc | gaatttggcg | ataccaaagt | gttgtgtacc | 120 |

```
gcctctattg aagaaggcgt gccgcgcttc ctgaaaggtc agggccaggg ctggatcacc      180
gcagagtacg gcatgctgcc acgttctacc cacacccgta acgctcgtga agcggcgaaa      240
ggtaagcagg gtggacgcac aatggaaatc cagcgtctga tcgcccgtgc tcttcgcgcg      300
gcagtagatt tgaaagcgct gggtgagttc accattacgc tggactgcga cgtgcttcag      360
gctgatggtg gcacgcgtac cgcgtcgatt acgggtgcct gcgtggcgct ggtagatgcg      420
ctacagaagc tggtggaaaa cggcaagctg aaaaccaatc cgatgaaagg gatggtagcc      480
gcagtttctg tcggaattgt gaacggcgaa gcggtttgcg atctggaata cgttgaagac      540
tctgccgcag agaccgacat gaacgtagtg atgaccgaag acgggcgcat cattgaagtg      600
caggggacgg cagaaggcgg cgctggcaaa ctgattttta aggcgactga tgagtcgcct      660 ttttttttgtc tgtagaaaag taagatgagg agcgaaggca tgaaaccata tcagcgccag      720
tttattgaat ttgcgcttag caagcaggta ttaaagtttg gcgagtttac gctgaaatcc      780
gggcgcaaaa gccctatttt cttcaacgcc gggctgttta taccgggcg cgatctggca      840 ctgttaggcc gttttacgc tgaagcgttg gtggattccg gcattgagtt cgatctgctg      900
tttggccctg cttacaaagg gatcccgatt gccaccacaa ccgctgtggc actggcggag      960
catcacgacc tggacctgcc gtactgcttt aaccgcaaag aagcaaaaga ccacggtgaa     1020
ggcggcaatc tggttggtag cgcgttacaa ggacgcgtaa tgctggtaga tgatgtgatc     1080
accgccggaa cggcgattcg cgagtcgatg gagattattc aggccaatgg cgcgacgctt     1140
gctggcgtgt tgatttcgct cgatcgtcag gaacgcgggc gcggcgagat ttcggcgatt     1200
caggaagttg agcgtgatta caactgcaaa gtgatctcta tcatcaccct gaaagacctg     1260
attgcttacc tggaagagaa gccggaaatg gcggaacatc tggcggcggt taaggcctat     1320
cgcgaagagt ttggcgttta a                                               1341

<210> SEQ ID NO 15
<211> LENGTH: 1740
<212> TYPE: DNA
<213> ORGANISM: artificial
<220> FEATURE:
<223> OTHER INFORMATION: chimeric DNA

<400> SEQUENCE: 15
tctagacgct caagttagta taaaaaagct gaacgagaaa cgtaaaatga tataaatatc       60
aatatattaa attagatttt gcataaaaaa cagactacat aatactgtaa aacacaacat      120
atgcagtcac tatgaatcaa ctacttagat ggtattagtg acctgtaaca gactgcagtg      180
gtcgaaaaaa aaagcccgca ctgtcaggtg cgggcttttt tctgtgttaa gcttcgacga      240
atttctgcca ttcatccgct tattatcact tattcaggcg tagcaccagg cgtttaaggg      300
caccaataac tgccttaaaa aaattacgcc ccgccctgcc actcatcgca gtactgttgt      360
aattcattaa gcattctgcc gacatggaag ccatcacaga cggcatgatg aacctgaatc      420
gccagcggca tcagcacctt gtcgccttgc gtataatatt tgcccatggt gaaaacgggg      480
gcgaagaagt tgtccatatt ggccacgttt aaatcaaaac tggtgaaact cacccaggga      540
ttggctgaga cgaaaaacat attctcaata aacccttttag ggaaataggc caggttttca      600
ccgtaacacg ccacatcttg cgaatatatg tgtagaaact gccggaaatc gtcgtggtat      660
tcactccaga gcgatgaaaa cgtttcagtt tgctcatgga aaacggtgta acaagggtga      720
acactatccc atatcaccag ctcaccgtct ttcattgcca tacggaattc cggatgagca      780
ttcatcaggc gggcaagaat gtgaataaag gccggataaa acttgtgctt attttttcttt      840
```

```
acggtctttta aaaaggccgt aatatccagc tgaacggtct ggttataggt acattgagca    900
actgactgaa atgcctcaaa atgttcttta cgatgccatt gggatatatc aacggtggta    960
tatccagtga ttttttctc cattttagct tccttagctc ctgaaaatct cggatccggc   1020
caagctagct tggctctagc tagagcgccc ggttgacgct gctagtgtta cctagcgatt   1080
tgtatcttac tgcatgttac ttcatgttgt caatacctgt ttttcgtgcg acttatcagg   1140
ctgtctactt atccggagat ccacaggacg ggtgtggtcg ccatgatcgc gtagtcgata   1200
gtggctccaa gtagcgaagc gagcaggact gggcggcggc caaagcgtc ggacagtgct   1260 ccgagaacgg gtgcgcatag aaattgcatc aacgcatata gcgctagcag cacgccatag   1320
tgactggcga tgctgtcgga atggacgata tcccgcaaga ggcccggcag taccggcata   1380
accaagccta tgcctacagc atccagggtg acggtgccga ggatgacgat gagcgcattg   1440
ttagatttca tacacggtgc ctgactgcgt tagcaattta actgtgataa actaccgcat   1500
taaagcttat cgatgataag ctgtcaaaca tgagaattcg aaatcaaata atgatttat   1560 tttgactgat agtgacctgt tcgttgcaac aaattgataa gcaatgcttt tttataatgc   1620
caacttagta taaaaaagca ggcttcaaga tctctcccca tcccctgtt ggcaattaat   1680 catcggctcg tataatgtgt ggaattgtga gcggataaca atttcacaca ggagactgcc   1740

<210> SEQ ID NO 16
<211> LENGTH: 2382
<212> TYPE: DNA
<213> ORGANISM: artificial
<220> FEATURE:
<223> OTHER INFORMATION: artificially modified pyrE gene

<400> SEQUENCE: 16
tctagacgct caagttagta taaaaaagct gaacgagaaa cgtaaaatga tataaatatc     60
aatatattaa attagatttt gcataaaaaa cagactacat aatactgtaa aacacaaacat   120 atgcagtcac tatgaatcaa ctacttagat ggtattagtg acctgtaaca gactgcagtg   180
gtcgaaaaaa aaagcccgca ctgtcaggtg cgggcttttt tctgtgttaa gcttcgacga   240
atttctgcca ttcatccgct tattatcact tattcaggcg tagcaccagg cgtttaaggg   300
caccaataac tgccttaaaa aaattacgcc ccgccctgcc actcatcgca gtactgttgt   360
aattcattaa gcattctgcc gacatggaag ccatcacaga cggcatgatg aacctgaatc   420
gccagcggca tcagcacctt gtcgccttgc gtataatatt tgcccatggt gaaaacgggg   480
gcgaagaagt tgtccatatt ggccacgttt aaatcaaaac tggtgaaact cacccaggga   540
ttggctgaga cgaaaaacat attctcaata aacccttag ggaaataggc caggttttca   600
ccgtaacacg ccacatcttg cgaatatatg tgtagaaact gccggaaatc gtcgtggtat   660
tcactccaga gcgatgaaaa cgtttcagtt tgctcatgga aaacggtgta acaagggtga   720
acactatccc atatcaccag ctcaccgtct ttcattgcca tacggaattc cggatgagca   780
ttcatcaggc gggcaagaat gtgaataaag gccggataaa acttgtgctt attttctttt   840 acggtctttta aaaaggccgt aatatccagc tgaacggtct ggttataggt acattgagca   900
actgactgaa atgcctcaaa atgttcttta cgatgccatt gggatatatc aacggtggta   960
tatccagtga ttttttctc cattttagct tccttagctc ctgaaaatct cggatccggc   1020
caagctagct tggctctagc tagagcgccc ggttgacgct gctagtgtta cctagcgatt   1080
tgtatcttac tgcatgttac ttcatgttgt caatacctgt ttttcgtgcg acttatcagg   1140
ctgtctactt atccggagat ccacaggacg ggtgtggtcg ccatgatcgc gtagtcgata   1200
```

```
gtggctccaa gtagcgaagc gagcaggact gggcggcggc caaagcggtc ggacagtgct    1260
ccgagaacgg gtgcgcatag aaattgcatc aacgcatata gcgctagcag cacgccatag    1320
tgactggcga tgctgtcgga atggacgata tcccgcaaga ggcccggcag taccggcata    1380
accaagccta tgcctacagc atccaggtg acggtgccga ggatgacgat gagcgcattg     1440
ttagatttca tacacggtgc ctgactgcgt tagcaattta actgtgataa actaccgcat    1500
taaagcttat cgatgataag ctgtcaaaca tgagaattcg aaatcaaata atgattttat    1560
tttgactgat agtgacctgt tcgttgcaac aaattgataa gcaatgcttt tttataatgc    1620
caacttagta taaaaaagca ggcttcaaga tctctcccca tcccctgtt ggcaattaat     1680 catcggctcg tataatgtgt ggaattgtga gcggataaca atttcacaca ggagactgcc    1740
atgaaaccat atcagcgcca gtttattgaa tttgcgctta gcaagcaggt gttaaagttt    1800
ggcgagttta cgctgaaatc cgggcgcaaa agccctatt tcttcaacgc cgggctgttt     1860
aataccgggc gcgatctggc actgttaggc cgttttacg ctgaagcgtt ggtggattcc     1920
ggcattgagt tcgatctgct gtttggccct gcttacaaag gatcccgat tgccaccaca     1980 accgctgtgg cactggcgga gcatcacgac ctggacctgc cgtactgctt taaccgcaaa    2040
gaagcaaaag accacggtga aggcggcaat ctggttggta gcgcgttaca aggacgcgta    2100
atgctggtag atgatgtgat caccgccgga acggcgattc gcgagtcgat ggagattatt    2160
caggccaatg gcgcgacgct tgctggcgtg ttgatttcgc tcgatcgtca ggaacgcggg    2220
cgcggcgaga tttcggcgat tcaggaagtt gagcgtgatt acaactgcaa agtgatctct    2280
atcatcaccc tgaaagacct gattgcttac ctggaagaga agccggaaat ggcggaacat    2340
ctggcggcgg ttaaggccta tcgcgaagag tttggcgttt aa                       2382
```

<210> SEQ ID NO 17
<211> LENGTH: 80
<212> TYPE: DNA
<213> ORGANISM: Artificial
<220> FEATURE:
<223> OTHER INFORMATION: primer

<400> SEQUENCE: 17

```
cgacgcagaa ggcggcgctg gcaaactgat ttttaaggcg actgatgagt tctagacgct    60
caagttagta taaaaaagct                                                80
```

<210> SEQ ID NO 18
<211> LENGTH: 79
<212> TYPE: DNA
<213> ORGANISM: Artificial
<220> FEATURE:
<223> OTHER INFORMATION: primer

<400> SEQUENCE: 18

```
ttgctaagcg caaattcaat aaactggcgc tgatatggtt tcatgccttc ctcctgtgtg    60
aaattgttat ccgctcaca                                                 79
```